US009898658B2

(12) United States Patent
Ebisawa

(10) Patent No.: US 9,898,658 B2
(45) Date of Patent: Feb. 20, 2018

(54) PUPIL DETECTION LIGHT SOURCE DEVICE, PUPIL DETECTION DEVICE AND PUPIL DETECTION METHOD

(71) Applicant: National University Corporation Shizuoka University, Shizuoka-shi, Shizuoka (JP)

(72) Inventor: Yoshinobu Ebisawa, Hamamatsu (JP)

(73) Assignee: NATIONAL UNIVERSITY CORPORATION SHIZUOKA UNIVERSITY (JP)

( * ) Notice: Subject to any disclaimer, the term of this patent is extended or adjusted under 35 U.S.C. 154(b) by 293 days.

(21) Appl. No.: 14/889,473

(22) PCT Filed: May 2, 2014

(86) PCT No.: PCT/JP2014/062183
§ 371 (c)(1),
(2) Date: Nov. 6, 2015

(87) PCT Pub. No.: WO2014/181775
PCT Pub. Date: Nov. 13, 2014

(65) Prior Publication Data
US 2016/0125241 A1 May 5, 2016

(30) Foreign Application Priority Data
May 8, 2013 (JP) ................................ 2013-098558

(51) Int. Cl.
*H04N 5/232* (2006.01)
*G06K 9/00* (2006.01)
(Continued)

(52) U.S. Cl.
CPC ........ *G06K 9/00604* (2013.01); *A61B 3/0008* (2013.01); *G06K 9/00255* (2013.01);
(Continued)

(58) Field of Classification Search
CPC ............ G06K 9/00604; G06K 9/00255; A61B 3/0008; A61B 3/113; A61B 3/11; G06T 7/77; G06T 2207/10152; H04N 5/23219
See application file for complete search history.

(56) References Cited

U.S. PATENT DOCUMENTS

2011/0069277 A1* 3/2011 Blixt ...................... A61B 3/113
351/210

FOREIGN PATENT DOCUMENTS

JP 2005-348832 A 12/2005
JP 2007-111315 A 5/2007
(Continued)

OTHER PUBLICATIONS

International Search Report for International Application No. PCT/JP2014/062183 dated Jun. 24, 2014.
(Continued)

*Primary Examiner* — Thai Tran
*Assistant Examiner* — Christopher T Braniff
(74) *Attorney, Agent, or Firm* — Ostrolenk Faber LLP

(57) ABSTRACT

A pupil detection light source device includes an aperture disposed to face a subject to allow light from a pupil of the subject to pass therethrough, an illumination light for obtaining a light pupil image toward the subject from the inside or the vicinity of the aperture when seen from the subject, and an illumination light for forming a reflection image with glasses obtained by canceling a reflection image with glasses of the light pupil image using an image difference toward the subject from the inside or the vicinity of the aperture when seen from the subject.

19 Claims, 16 Drawing Sheets

(51) Int. Cl.
- *A61B 3/00* (2006.01)
- *A61B 3/11* (2006.01)
- *A61B 3/113* (2006.01)
- *G06T 7/77* (2017.01)

(52) U.S. Cl.
CPC ........... *G06T 7/77* (2017.01); *H04N 5/23219* (2013.01); *A61B 3/11* (2013.01); *A61B 3/113* (2013.01); *G06T 2207/10152* (2013.01)

(56) References Cited

FOREIGN PATENT DOCUMENTS

| | | |
|---|---|---|
| JP | 2008-125619 A | 6/2008 |
| JP | 2008-132160 A | 6/2008 |
| JP | 2008-246004 A | 10/2008 |
| JP | 2009-254525 A | 11/2009 |
| JP | 4491604 B2 | 6/2010 |
| JP | 4528976 B2 | 8/2010 |
| JP | 4528980 B2 | 8/2010 |
| JP | 4613315 B2 | 1/2011 |
| JP | 2014-052813 A | 3/2014 |

OTHER PUBLICATIONS

PCT/IB/338 Form PCT Notification of Transmittal of Translation of the International Preliminary Report on Patentability with Form PCT/ISA/237 PCT Translation of Written Opinion of the International Searching Authority dated Nov. 19, 2015.
Extended European Search Report dated Jan. 5, 2017 for European Application No. 14795046.3.

* cited by examiner

Fig.2
(a) 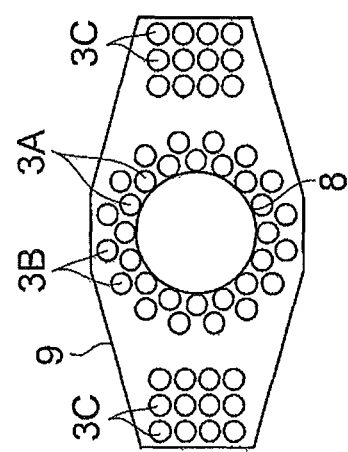
(b) 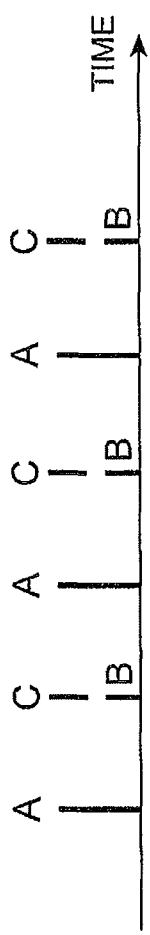

Fig.13
(a) 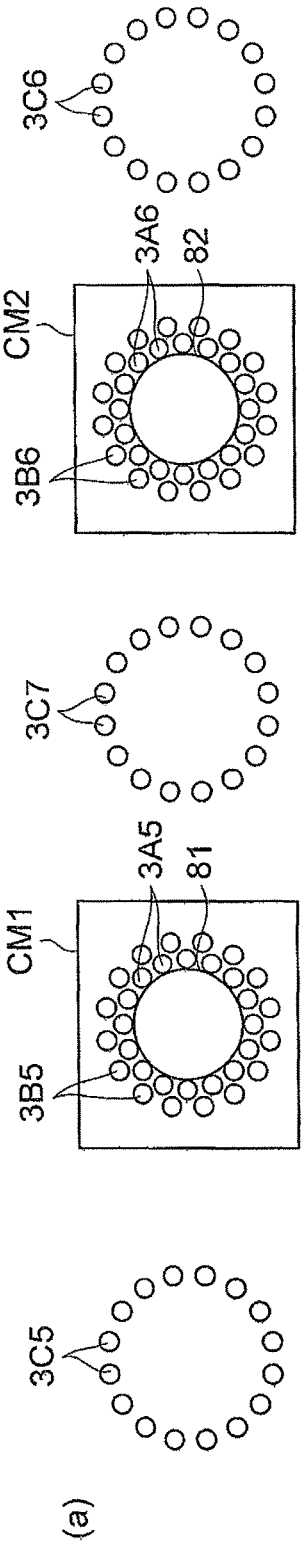
(b) 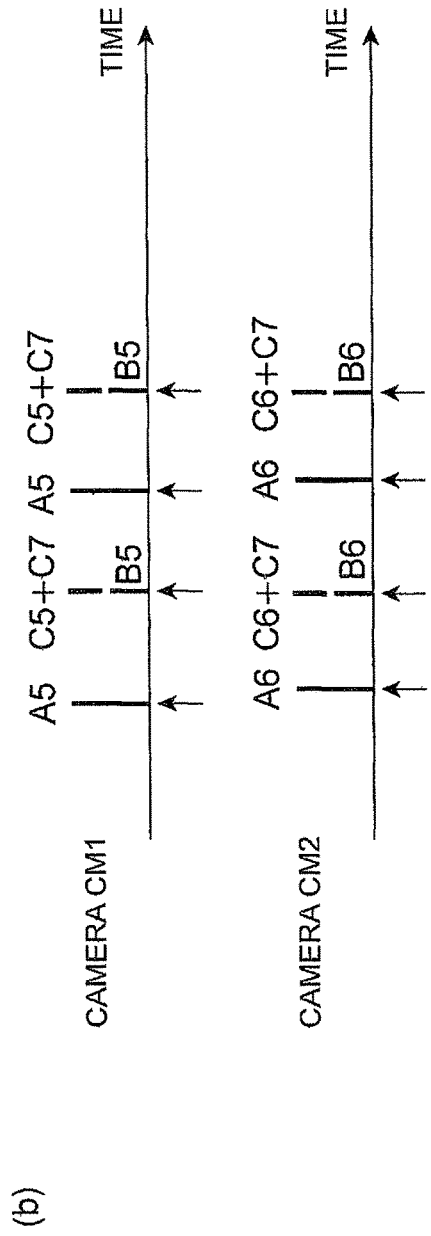

PUPIL DETECTION LIGHT SOURCE DEVICE, PUPIL DETECTION DEVICE AND PUPIL DETECTION METHOD

TECHNICAL FIELD

The present invention relates to a pupil detection light source device, a pupil detection device, and a pupil detection method, which detect a pupil of a subject by using a captured image.

BACKGROUND ART

A technique for detecting the pupils of a subject can be used for line-of-sight detection in order for intension expression of a physically ahandicapped person or opinion communication in an environment where information communication by voice is difficult. The line-of-sight detection is generally performed by calculating a relative position between a center of a pupil taken by a camera and corneal reflection obtained by illumination light from a light source. Also, it has been studied that the pupil detection technique is applied to a pupil mouse that performs input to a computer or a game apparatus by movement of a pupil of a subject without using fingers, or the pupil detection technique is used for doze prevention technique or driving management technique in automotive technology.

As an example of such a pupil detection technique, the following Patent Literature 1 discloses a pupil detection device as follows. The pupil detection device includes a light source which irradiates with illumination light and a camera which picks up a light pupil image and a dark pupil image of a subject. The camera has a aperture disposed to face the subject to allow an image of the subject to be introduced to an imaging element, and the light source includes first light-emitting elements which are arranged along edges of the aperture on the outside of the aperture and emit illumination light having a first central wavelength and second light-emitting elements which are arranged adjacent to the outsides of the first light-emitting elements and has a second central wavelength longer than the first central wavelength. By using such a pupil detection device, the light pupil image is picked up while irradiating the subject with illumination light by the first light-emitting elements, the dark pupil image is picked up while irradiating the subject with illumination light by the second light-emitting elements, and a difference between the light pupil image and the dark pupil image is calculated. Since pixel values at a position of the pupil of the subject in the light pupil image and the dark pupil image are significantly different from each other and differences in pixel values at positions other than the pupil of the subject are small, it is possible to detect the position of the pupil of the subject by calculating a difference in pixel values between the light pupil image and the dark pupil image.

There has been known various arrangements of light sources in the pupil detection technique using the light pupil image and the dark pupil image. For example, in a pupil detection device described in the following Patent Literature 2, a light source capable of irradiating with light from the inside of an aperture of a camera is provided, the light source includes a first illumination light source, having a first wavelength component that makes a bright pupil by reflection in a subject's pupil, and a second illumination light source having a second wavelength component that makes a dark pupil by reflection in the subject's pupil, and change of optical paths are made such that independent optical axes of the first illumination light source and the second illumination light source both coincide with an optical axis of camera means.

In a pupil detection device described in the following Patent Literature 3, light from a first illumination light source, having a first wavelength component that makes a bright pupil by reflection in a subject's pupil is emitted from the inside of an aperture when seen from a face side of the subject, and light from a second illumination light source, having a second wavelength component that makes a dark pupil by reflection in the subject's pupil is emitted from a plurality of positions which are adjacent to the outer periphery of the aperture and are rotationally symmetric to each other.

In a pupil detection device described in the following Patent Literature 4, a plurality of light-emitting elements are arranged along edges of an aperture of a camera, and the light-emitting elements include a first light emission source which emits illumination light having a first central wavelength and a second light emission source which emits illumination light having a second central wavelength longer than the first central wavelength.

CITATION LIST

Patent Literature

Patent Literature 1: Japanese Patent Application Laid-Open No. 2008-125619
Patent Literature 2: Japanese Patent No. 4528980
Patent Literature 3: Japanese Patent No. 4613315
Patent Literature 4: Japanese Patent Application Laid-Open No. 2008-132160

SUMMARY OF INVENTION

Technical Problem

On the other hand, in a case where a subject uses glasses, a shape or position of a reflection image with glasses generated in such a way that light emitted by a light source is reflected by a prism or frame of the glasses of the subject depends on a shape or position of the light source. Therefore, when a shape or position of the first light-emitting elements are different from a shape or position of the second light-emitting elements, reflection image with glasses by the first and second light sources becomes different from each other in their shape and position. In this case, although differential processing has been performed, a part of the reflection image with glasses is left, and it is apprehended that the left part is likely to be erroneously detected as a pupil.

The arrangements of light sources in the pupil detection device in the aforementioned Patent Literatures 1 to 4 have the following problems respectively. In the pupil detection device disclosed in the Patent Literature 1, when the second light emission source is disposed adjacent to the first light emission source, a difference in brightness between the bright pupil and the dark pupil is small On the other hand, when the second light emission source is disposed spaced apart from the first light emission source, a difference in brightness between the bright pupil and the dark pupil is large, but it is difficult to cancel the reflection image with glasses when a difference of pixel values between the light pupil image and the dark pupil image is calculated, so that it becomes easier to erroneously detect remains of the reflection image with glasses as the pupil of the subject. In the pupil detection devices disclosed in Patent Literatures 2 and 3, it is difficult to configure optical path change for allowing light to be emitted from the inside of the aperture in the light source, and also, a brightness difference between the bright pupil and the dark pupil is small In the pupil detection device disclosed in Patent Literature 4, a brightness difference between the bright pupil and the dark pupil is small, and also, it is hard to increase the number of light emission sources capable of being arranged since the first and second light emission sources are arranged in a line in the vicinity of the aperture. In particular, since the brightness of each of the second light emission sources which emit illumination light having the second central wavelength is less than half the brightness of each of the first light emission sources which emit illumination light having the first central wavelength, it is necessary to reduce the number of the first light emission sources when it is attempted to dispose second light emission sources of which the number is sufficient to ensure brightness, and, as a result, it is difficult to emit light having a light quantity to an extent capable of detecting the pupil of the subject.

The present invention has been made in an effort to solve the above-described problems and an object of the present invention is to provide a pupil detection light source device, a pupil detection device, and a pupil detection method, which are capable of expanding or maintaining a brightness/darkness difference between a light pupil image and a dark pupil image, and at the same time, removing a reflection image with glasses.

Solution to Problem

To solve the above problems, a pupil detection light source device according to one aspect of the present invention is used for detecting a pupil of a subject based on a light pupil image and a dark pupil image of the subject, the pupil detection light source device irradiating toward a face of the subject with illumination light for obtaining the light pupil image and the dark pupil image, and including an aperture disposed to face the subject to allow light from a pupil of the subject to pass therethrough, and provided in a camera, a first light source configured to irradiate toward a face of the subject with illumination light for obtaining the light pupil image by the camera from at least one of inside or vicinity of the aperture when seen from the subject, a second light source configured to irradiate toward the face of the subject with illumination light for forming a reflection image with glasses to an extent capable of canceling the reflection image with glasses of the subject in the light pupil image obtained by the camera by using an image difference, from a position which exists in at least one of the inside or the vicinity of the aperture when seen from the subject, and at which a distance from a center of the aperture is equal or large in comparison to a position of the first light source, and a third light source configured to irradiate toward the face of the subject with illumination light for obtaining the dark pupil image by the camera from a position spaced apart from the aperture when seen from the subject.

According to the pupil detection light source device according to one aspect of the present invention, illumination light for obtaining the light pupil image is emitted toward the subject from the inside or the vicinity of the aperture by the first light source, and illumination light for obtaining the dark pupil image is emitted toward the subject from the inside or the vicinity of the aperture by the second light source, and, illumination light for obtaining the dark pupil image is emitted from a position spaced apart from the aperture by the third light source. Therefore, by picking up the light pupil image when illumination light is emitted by the first light source and picking up the dark pupil image when illumination light is emitted by the second light source and the third light source, it is possible to expand a difference in brightness between the light pupil image and the dark pupil image by the first light source and the third light source. At the same time, the second light source can generate a reflection image with glasses having brightness, a size, and a shape to an extent capable of canceling or removing the reflection image with glasses by the first light source using an image difference, and it is possible to remove the reflection image with glasses using the difference by taking a difference between the light pupil image and the dark pupil image which are picked up and detect the pupil of the subject more conspicuously.

Also, a pupil detection device according to one aspect of the present invention includes the aforementioned pupil detection light source device; imaging unit configured to image a light pupil image and a dark pupil image of the subject obtained by illumination light emitted by the pupil detection light source device; and pupil detection unit configured to detect a pupil of the subject based on the light pupil image and the dark pupil image, wherein the imaging unit has an imaging element configured to image the light pupil image and the dark pupil image and output image data, and an optical system configured to form the light pupil image and the dark pupil image toward the imaging element.

According to the pupil detection device according to one aspect of the present invention, by picking up the light pupil image by the imaging unit when illumination light is emitted by the first light source and picking up the dark pupil image when illumination light is emitted by the second light source and the third light source, it is possible to expand a difference in brightness of a pupil portion between the light pupil image and the dark pupil image by the first light source and the third light source. At the same time, since the second light source can generate a reflection image with glasses having brightness, a size, and a shape to an extent capable of canceling or removing the reflection image with glasses by the first light source using an image difference, it is possible to remove the reflection image with glasses by taking a difference between the light pupil image and the dark pupil image using an image difference, thereby making it easy to detect the pupil.

A pupil detection method according to one aspect of the present invention, uses the aforementioned pupil detection light source device, and includes a step of picking up a light pupil image and a dark pupil image of a subject obtained by illumination light emitted by the pupil detection light source device; and a step of detecting a pupil of the subject based on the light pupil image and the dark pupil image.

According to the pupil detection method according to an aspect of the present invention, by picking up the light pupil image by the imaging unit when illumination light is emitted by the first light source and picking up the dark pupil image when illumination light is emitted by the second light source and the third light source, it is possible to expand a difference in brightness of a pupil portion between the light pupil image and the dark pupil image by the first light source and the third light source. At the same time, since the second light source can generate a reflection image with glasses having brightness, a size, and a shape to an extent capable of canceling or removing the reflection image with glasses by the first light source using an image difference, it is possible to take the difference between the light pupil image and the dark pupil image, thereby making it easy to detect the pupil.

Also, as to a bright pupil and a dark pupil in this specification, with respect to the bright pupil, an image of the pupil portion is not necessarily brighter than neighboring images and, with respect to the dark pupil, an image of the pupil portion is limited to be darker than neighboring images, according to a condition, such as the brightness of the surroundings or the like. In the present specification, the bright pupil and the dark pupil represent a relative difference in brightness between pupils of two captured images. The bright pupil is relatively brighter than the dark pupil.

Advantageous Effects of Invention

According to the pupil detection light source device, the pupil detection device, and the pupil detection method of the present invention, it is possible to expand brightness/darkness difference between a light pupil image and a dark pupil image, and at the same time, remove a reflection image with glasses.

BRIEF DESCRIPTION OF DRAWINGS

FIG. 2 is a diagram illustrating a configuration and a light emission timing of a pupil detection light source device according to a first embodiment of the present invention.

FIG. 13 is a diagram illustrating a light emission timing and an image timing of a pupil detection light source device according to still another modification example of the second embodiment of the present invention.

DESCRIPTION OF EMBODIMENTS

Figure 1:
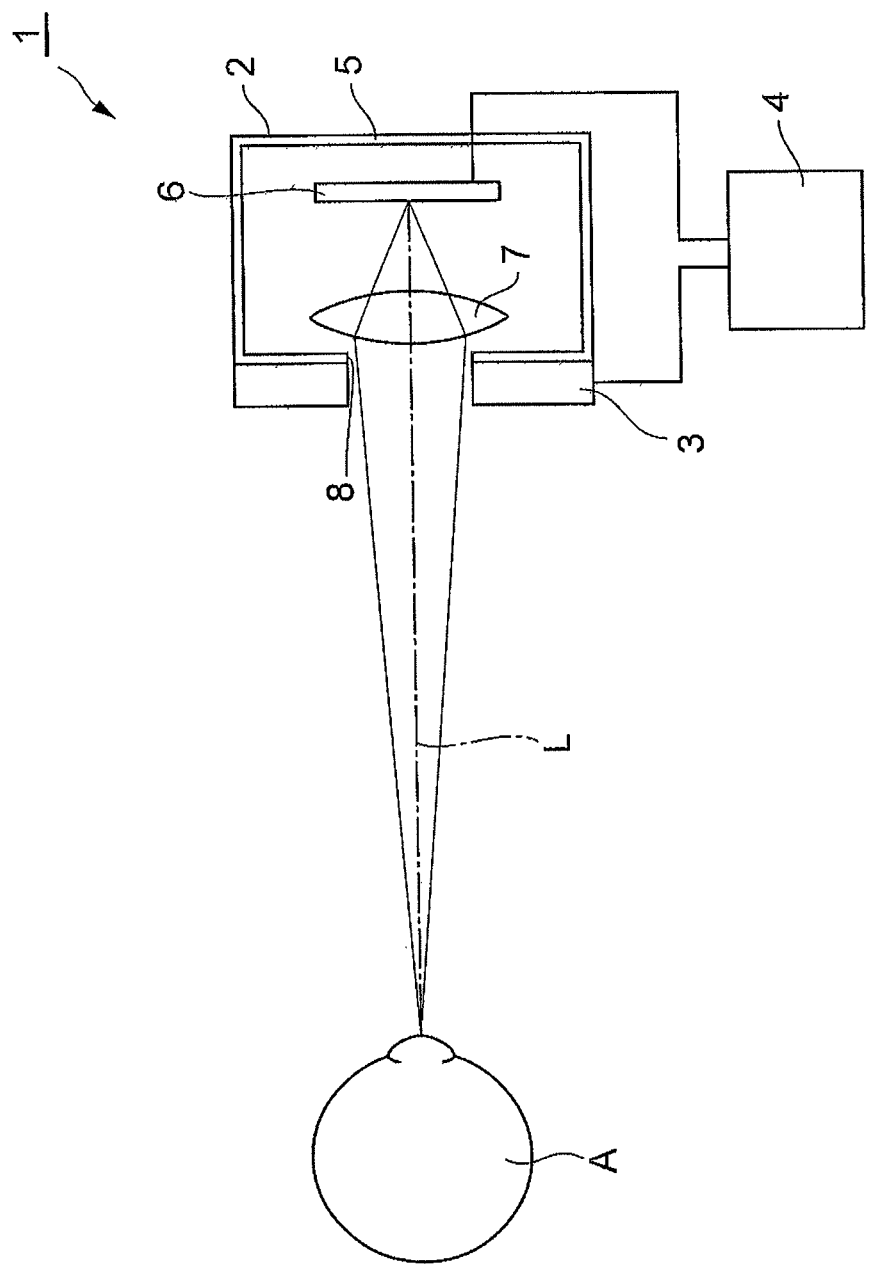
FIG. 1 is a conceptual diagram schematically illustrating a configuration of a pupil detection device according to a first embodiment of the present invention.

Hereinafter, preferred embodiments of a pupil detection light source device, a pupil detection device, and a pupil detection method according to the present invention will be described hereinafter in detail with reference to the drawings. Note that, in the description of the drawings, the same or equivalent elements are denoted by the same reference numerals and a redundant description thereof is omitted.

(First Embodiment)

FIG. 1 is a conceptual diagram schematically illustrating a configuration of a pupil detection device according to a first embodiment of the present invention. As illustrated in this drawing, a pupil detection device 1 includes a camera 2 as imaging unit, a light source 3 as a pupil detection light source device, and a control device 4 as a control unit.

The camera 2 is configured in such a way that an imaging element 6, such as a CCD or a CMOS, and an objective lens 7 are accommodated in a housing 5. An aperture 8 having a circular shape is formed in a surface of the housing 5 to face an eyeball A of a subject to be observed. The objective lens 7 is disposed such that an optical axis thereof is coincide with a central axial line of the aperture 8 between the aperture 8 and the imaging element 6, and the imaging element 6 is fixed such that a light receiving surface thereof perpendicularly intersects with the optical axis L of the objective lens 7. Also, a diameter of the aperture 8 is smaller than a diameter of the objective lens 7 and is approximately equal to an effective diameter of the objective lens 7. Due to the aforementioned configuration, an image in the proximity of the eyeball A of the subject is introduced toward the imaging element 6 of the camera 2 through the aperture 8, and thereafter, is formed so as to converge on the light receiving surface of the imaging element 6 by an optical system including the objective lens 7 of the camera 2.

The imaging element 6 generates image data by picking up an image of the eyeball A of the subject and outputs the image data to the control device 4. The control device 4 controls a light emission intensity and a light emission timing of the light source 3, and an image timing of the camera 2. In addition, the control device 4 functions as pupil detection unit by performing differential processing and pupil detection processing based on an image output from the imaging element 6.

FIG. 2(a) illustrates a plan view of the light source 3 of FIG. 1 when seen from the outside of the housing 5. The light source 3 emits illumination light toward the face of a subject, and has a structure in which respective three groups of light-emitting elements 3A (first light source), light-emitting elements 3B (second light source), and light-emitting elements 3C (third light source) are embedded in a casing 9 that accommodates the light source 3. The casing 9 of the light source 3 is attached so as to cover the outside of the aperture 8 in a surface of the housing 5 along edges of the aperture 8.

The light-emitting elements 3A are light sources for irradiating toward the face of a subject with illumination light for obtaining a light pupil image. The light pupil image refers to an image in which a pupil of the subject is reflected relatively brightly in comparison to a dark pupil image to be described below. The light-emitting elements 3A include a plurality of semiconductor light-emitting elements (LED) in which output light has a central wavelength of 850 nm (first central wavelength), and are disposed in the vicinity of the aperture 8. Specifically, the light-emitting elements 3A are arranged in a ring shape at equal intervals along the edges of the aperture 8 on the outside of the aperture 8 on the casing 9. It is preferable that the light-emitting elements 3A are disposed at positions as close as possible to the edges of the aperture 8. Therefore, as described below, a pupil is more brightly reflected and a small pupil is also easily detected in an image of a subject illuminated by the light-emitting elements 3A.

The light-emitting elements 3B are light sources that irradiate toward the face of the subject with illumination light for forming a reflection image with glasses to an extent capable of canceling the glasses-reflective image of the subject by an image difference in a light pupil image obtained by irradiation with the illumination light from the light-emitting elements 3A. The light-emitting elements 3B include a plurality of LEDs in which output light has a central wavelength of 950 nm (second central wavelength), and are disposed in the vicinity of the aperture 8. Specifically, the light-emitting elements 3B are arranged in a ring shape at equal intervals adjacent to the outsides of the light-emitting elements 3A on the casing 9. The number of the light-emitting elements 3B is equal to or greater than the number of the light-emitting elements 3A. The numbers of the light-emitting elements 3A and the light-emitting elements 3B are determined so as to achieve a balance of illuminance in the face of the subject, that is, such that the illuminance in the face of the subject in a case where illumination light is emitted to the face of the subject by the light-emitting elements 3A is approximately equal to the illuminance in the face of the subject in a case where illumination light is emitted to the face of the subject by the light-emitting elements 3B. In order to achieve the balance of illuminance, generally, it is necessary to increase the number of the light-emitting elements 3B, rather than the number of the light-emitting elements 3A. For example, the number of the light-emitting elements 3B is about two times or three times the number of the light-emitting elements 3A. However, a ratio of the number of the light-emitting elements 3B to the number of the light-emitting elements 3A is not limited to the aforementioned value.

The light-emitting elements 3C are light sources for irradiating toward the face of the subject with illumination light for obtaining a dark pupil image. The dark pupil image refers to an image in which a pupil of the subject is reflected relatively darkly in comparison to the aforementioned light pupil image. The light-emitting elements 3C include a plurality of LEDs arranged to be spaced apart from the light-emitting elements 3B on the outside of the aperture 8 on the casing 9. In this case, with respect to how far the light-emitting elements 3B is spaced apart from the light-emitting elements 3C, a difference in angle when seen from the subject between the light-emitting elements 3B and the light-emitting elements 3C is more important than a distance between the light-emitting elements 3B and the light-emitting elements 3C. That is, when a distance between the pupil detection device 1 and the eyeball A of the subject is large, it is necessary to increase the distance between the light-emitting elements 3B and the light-emitting elements 3C in the pupil detection device 1, in comparison to a case where a distance between the pupil detection device 1 and the eyeball A of the subject is small. Specifically, it is preferable that an angle between the light-emitting elements 3B and the light-emitting elements 3C when seen from the subject, that is, an angle between a straight line connecting the eyeball A of the subject and the light-emitting elements 3B and a straight line connecting the eyeball A of the subject and the light-emitting elements 3C is, for example, about 3°.

Like the light-emitting elements 3B, the light-emitting elements 3C emit illumination light having a central wavelength of 950 nm toward the subject. Also, the plurality of LEDs constituting the light-emitting elements 3C are arranged at symmetric positions with the aperture 8 being interposed therebetween such that they are divided into two groups. In addition, although the light-emitting elements 3C are arranged as a pair of light source groups which are divided with the aperture 8 being interposed therebetween in the present embodiment, it may be possible to arrange two or more pairs of light sources arranged in different directions with the aperture 8 as a center, on the casing 9. The central wavelength of the illumination light emitted from the light-emitting elements 3C is preferably 950 nm, but may be 850 nm or other wavelength value or may be invisible near infrared light.

However, it is preferable that the central wavelength of the illumination light emitted by the light-emitting elements 3C is in a range of 800 nm to 1000 nm.

Also, generally, a sensitivity of a commercial camera decreases in a near infrared region due to an optical filter attached to an image sensor surface, in comparison to visible light. As the wavelength increases even in the near infrared region, the sensitivity further decreases. Therefore, a sensitivity of the camera also decreases in a case where the wavelength is 950 nm, for example, in comparison to a case where the wavelength is 850 nm. Further, since a power of the LED itself also decreases when the wavelength becomes longer, in order to make brightness of the face image reflected on a camera image uniform, more LEDs are needed as the wavelength becomes longer in the aforementioned wavelength range of 800 nm to 1000 nm. Conversely, in order to reduce the use number of LEDs, a short wavelength may be selected.

The aforementioned range of 800 nm to 1000 nm is determined due to the following reason. A wavelength of light emitted by the LED is not a single wavelength as in a laser, a large width exists in a light emission wavelength. Therefore, although a central wavelength of the LED is in the range of 800 nm to 1000 nm, visible light having a short wavelength is included in the light emitted by the LED. Accordingly, when a light-emitting element (for example, a super luminescence diode or the like) in which a half value width is narrower than the LED as a light-emitting element, there may be a range wider than the range of 800 nm to 1000 nm.

By the aforementioned arrangement of the light-emitting elements 3A, 3B, and 3C, a distance from the optical axis L of the light-emitting elements 3B is set to be larger than a distance from the optical axis L of the light-emitting elements 3A, and a distance from the optical axis L of the light-emitting elements 3C is set to be larger than the distance from the optical axis L of the light-emitting elements 3B. In this case, the light-emitting elements 3A, 3B, and 3C are provided on the casing 9 so as to emit the illumination light along the optical axis L of the objective lens 7. Also, the number of the light-emitting elements 3A, 3B, and 3C and a current to be supplied thereto respectively are set to an appropriate number and a current value such that a light emission intensity of the light-emitting elements 3A is equal to the sum of a light emission intensity of the light-emitting elements 3B and a light emission intensity of the light-emitting elements 3C. That is, the light emission intensities of the light-emitting elements 3A, 3B, and 3C are set such that the illuminance in the face of the subject which is a capturing object in the case of allowing the light-emitting elements 3A to emit light is equal to the illuminance in the face in the case of allowing the light-emitting elements 3B and the light-emitting elements 3C to emit light. Also, the light emission timings of the light-emitting elements 3A, 3B, and 3C are respectively controllable in an independent manner by a control signal from the control device 4.

In this case, when illumination light is emitted from the light-emitting elements 3A of the light source 3 to the eyeball A of the subject, a light pupil image is generated in the eyeball A, and when illumination light is emitted simultaneously from the light-emitting elements 3B and the light-emitting elements 3C, a dark pupil image is generated in the eyeball A. This is due to a synergistic effect of the following two properties. A first property is that, in a case where the eyeball A receives illumination light having a wavelength shorter than 900 nm, the illumination light is hardly absorbed by a medium constituting the eyeball A, the pupil is more brightly reflected compared to the case of receiving illumination light having a wavelength longer than 900 nm. A second property is that, in a case where illumination light directed to the eyeball A is incident from a position spaced apart from the optical axis of the camera 2, the illumination light, which is reflected by the inside of the eyeball and again transmits the pupil, hardly reaches the camera 2, and therefore, the pupil is darkly reflected.

Also, the light-emitting elements 3A, 3B, and 3C are not limited to a light-emitting element in which a central wavelength of output light is the aforementioned wavelength. As the light-emitting elements 3B and 3C, it is possible to use of a light-emitting element in which a central wavelength is 930 nm, 940 nm, or 970 nm instead of a light-emitting element in which a central wavelength is 950 nm. As the light-emitting element 3A, it is possible to use of a light-emitting element in which a central wavelength is 880 nm instead of a light-emitting element in which a central wavelength is 850 nm. In such a way, it is possible to use a light-emitting element having an arbitrary central wavelength with about 900 nm as a boundary. Also, as the light-emitting element 3C, it is possible to use a light-emitting element having another central wavelength, rather than use a light-emitting element having the same central wavelength as the light-emitting element 3B. To the last, in a case where the light emission intensities of the light-emitting elements are adjusted (that is, balance is achieved) such that the same brightness is obtained in a face area of the subject in a camera image when the light-emitting elements 3A, 3B, and 3C are disposed at the same position, it is preferable that a bright pupil becomes brighter than a dark pupil, and a relevant wavelength corresponds thereto. However, use of a light-emitting element having a central wavelength less than 850 nm as the light-emitting elements 3A, 3B, and 3C is not preferable since the light source itself shines to cause the subject to be dazzled and feel uncomfortable, and at the same time, there occurs influence where the illuminated pupil of the subject contracts, or the like. Also, since the light source may be visible in red although the subject does not completely recognize light itself which is emitted by the light-emitting element when a light-emitting element having a central wavelength of 850 nm is used, there is a case where it is preferable to select a wavelength of about 870 nm, as an inappropriate use.

Figure 3:
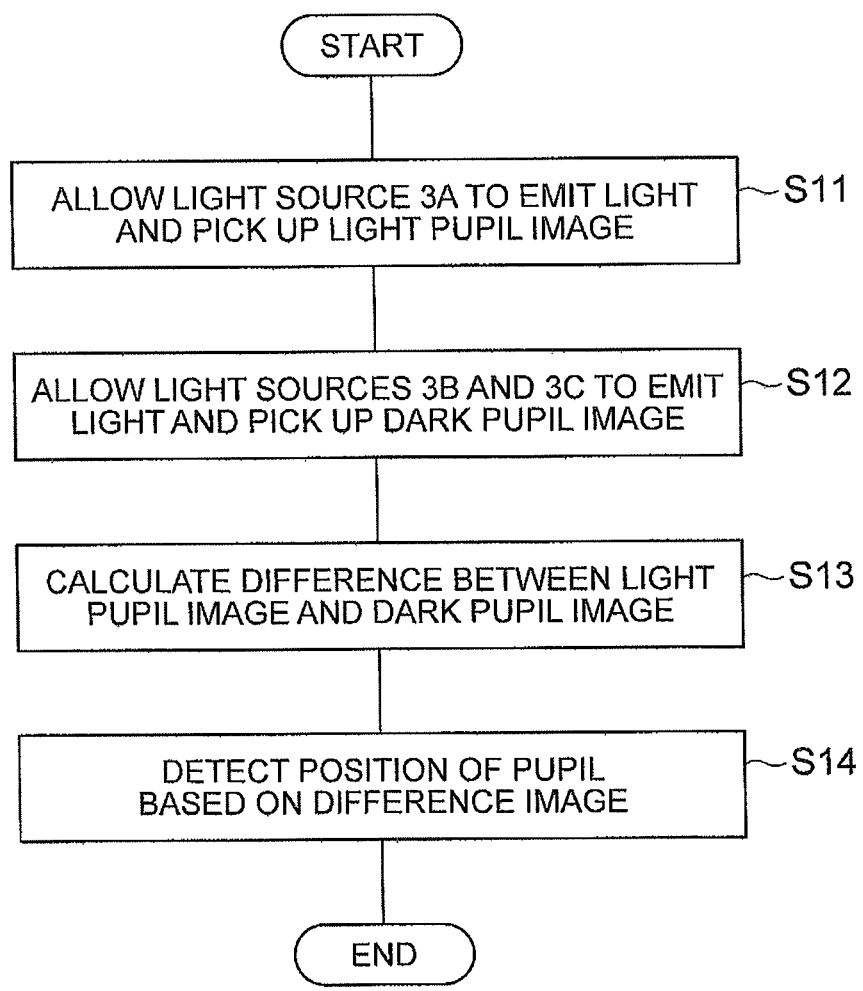
FIG. 3 is a flowchart of a pupil detection method according to a first embodiment of the present invention.

Next, an operation of the pupil detection device 1 according to a first embodiment of the present invention will be described and a pupil detection method according to a first embodiment will be described. FIG. 2(b) is a schematic diagram illustrating a light emission timing of the light sources 3A, 3B, and 3C, and FIG. 3 is a flowchart of the pupil detection method according to the present embodiment.

First, in a state in which the camera 2 is disposed such that the aperture 8 faces a subject, the control device 4 allows the light sources 3A to emit light at a first time point and, picks up an image of an eyeball A of the subject by the imaging element 6 (step S11). At this time, a light pupil image of the subject is picked up by illumination light from the light-emitting elements 3A. Subsequently, the control device 4 allows the light-emitting elements 3B and 3C to emit light at a second time point which is different from the first time point, and, picks up an image of the eyeball A of the subject by the imaging element 6 (step S12). At this time, a dark pupil image of the subject is picked up by illumination light from the light-emitting elements 3B and 3C.

Next, the control device 4 calculates a difference between the light pupil image and the dark pupil image picked up in steps S11 and S12 and generates a difference image (step S13). The control device 4 detects a position of a pupil of the subject based on the difference image (step S14). Thereafter, the pupil detection device 1 repeatedly performs the aforementioned steps S11 to S14 at a constant period. In addition, FIG. 2(b) is a diagram illustrating a light emission timing of respective light sources in the aforementioned pupil detection method. The light-emitting elements 3A are lit at a timing A of FIG. 2(b), and the light-emitting elements 3B and 3C are simultaneously lit at timings B and C of FIG. 2(b). In FIG. 2(b), a length of a bar represents a degree of influence on brightness in the face of the subject on the camera image. The lengths of bar B and bar C both are about half the length of bar A. This represents that the influence on the brightness of the face of the subject due to the light-emitting elements 3B and the light-emitting elements 3C is about half the influence on the brightness of the face of the subject due to the light-emitting elements 3A. In other words, the sum of the influence on the brightness of the face of the subject due to the light-emitting elements 3B and the light-emitting elements 3C is about equal to the influence on the brightness of the face of the subject due to the light-emitting elements 3A.

According to the pupil detection device 1 described above, illumination light having a central wavelength of 850 nm is emitted toward the subject from the light-emitting elements 3A arranged along the edges of the aperture 8 and illumination light having a central wavelength of 950 nm longer than 850 nm is emitted toward the subject from the light-emitting elements 3B adjacent to the outsides of the light-emitting elements 3A. At the same time, illumination light is emitted toward the subject from the light-emitting elements 3C arranged to be spaced apart from the light-emitting elements 3B on the outside of the aperture. Therefore, when a face image of the subject is picked up by light passing through the aperture 8, reflected light from the pupil of the subject becomes strong by two reasons of the fact that a reflected light becomes stronger as much as light from a light source adjacent to the aperture in a case where the illumination light is emitted by the light-emitting elements 3A, in comparison to a case where the illumination light is emitted by the light-emitting elements 3B and the light-emitting elements 3C, and the fact that light having a short wavelength is different to be absorbed by a medium constituting an eyeball in comparison to light having a long wavelength. On the other hand, in the reflection image with glasses, brightness is extremely strong in the face of the subject, such as a face or a pupil, compared to other portions than glass reflection. Therefore, when an iris or gain of the camera and a light quantity of a light-emitting element are adjusted so as to reflect the face brightly to some extent in order to facilitate pupil detection, brightness in a portion of glass reflection is saturated. That is, with respect to an image in which almost all pixel values of a face area are expressed with less than 125 (hereinafter referred to as a first image), a glass reflection peak is to represent a value of about 1000, but, when the maximum value of a pixel value is 255, it means that almost all of glasses reflection represent the maximum value of 255, that is, are saturated. When another image (hereinafter referred to as a second image) is obtained by reducing the light quantity of the light-emitting element in the case of obtaining the first image by half, the pixel value in the face area is half the pixel value of the first image in a case where external light does not exist. However, since a peak of glass reflection still represents a value of about 500 that is half the first image, many portions of glass reflection become narrower somewhat than the case of the first image, but represent the maximum value 255 and are saturated. Therefore, when a difference between the first image and the second image is obtained, a pixel value of a glass reflection portion that is being saturated becomes zero. As described above, the fact that a pixel of glass reflection is saturated is important in cancelation of glass reflection using image difference.

In addition, in the case of obtaining the second image, another light source is lit at a different position and a light quantity of the light source is adjusted such that a pixel value in the face area of the second image is equal to a pixel value in the face area of the first image. Then, the pixel value in the face area of the second image is added to the pixel value of the reflection image with glasses in the face area of the second image, and therefore, the reflection image with glasses of the second image is easily saturated. As described above, since it is possible to prevent an area in which the pixel value of glasses reflection is saturated from being narrow, glasses reflection is easily canceled in the case of taking a difference between the first image and the second image. In this case, when a position and a wavelength of each light source are given such that a bright pupil is obtained in the first image and a dark pupil is obtained in a subsequent image, in the case of obtaining a difference image by subtracting the second image from the first image, pixel values in the face area and glasses-reflected portion of the difference image become zero, and pixel values in the pupil area only represent values larger than zero, thereby detecting the pupil portion by binarization.

Figure 4:
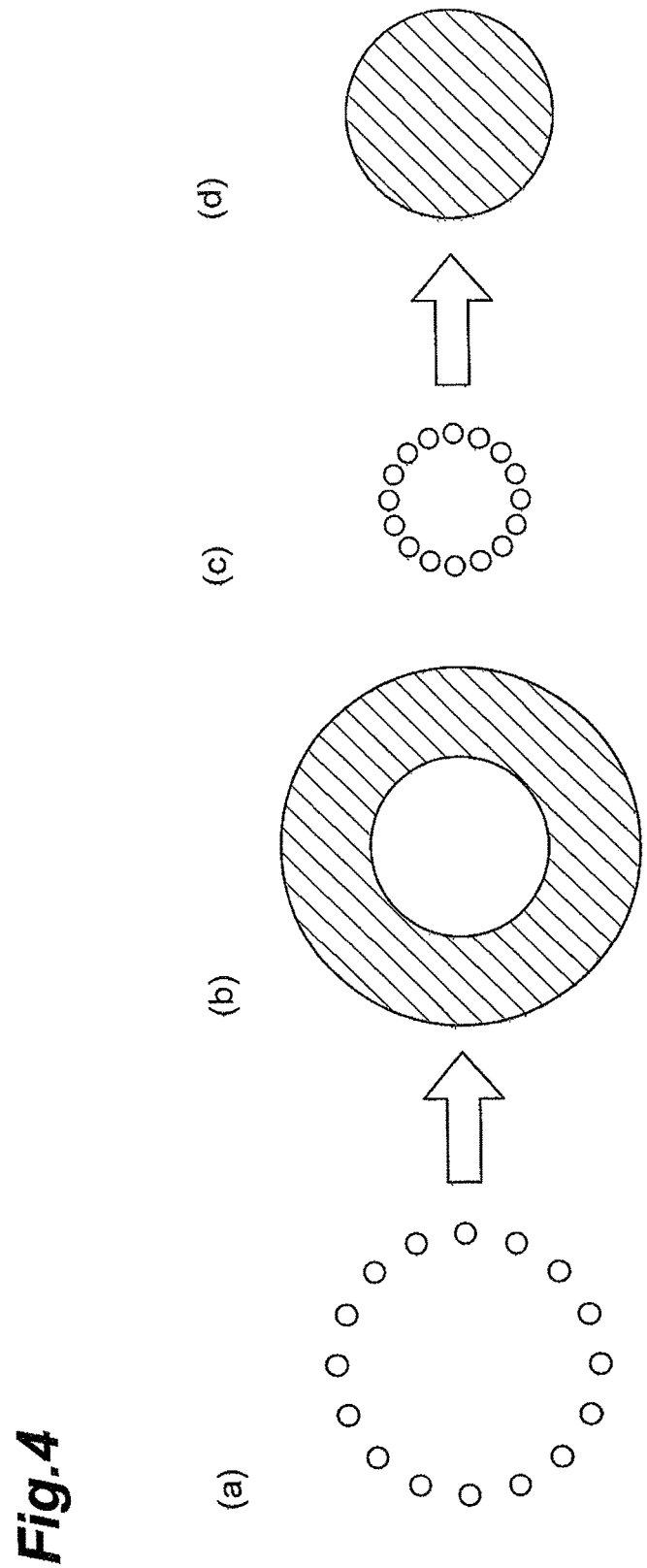
FIG. 4 is a schematic diagram illustrating a shape of a light source and a shape of a reflection image with glasses generated by the light source.

In addition, an image of glass reflection is reflected in a shape in which each of light-emitting elements constituting a light source is expanded as it is and is largely swollen, rather than is reflected as a reflection image with glasses. When a plurality of light-emitting elements are arranged at equal intervals in a circular shape as illustrated in FIG. 4(a), the image of glasses reflection has a shape which is swollen in a doughnut shape as illustrated in FIG. 4(b). When, as illustrated in FIG. 4(c), a plurality of light-emitting elements are arranged in a circular shape having a radius smaller than that of FIG. 4(a), the image of glasses reflection has a circular shape in which an inner portion of the doughnut shape of FIG. 4(b) is filled up as illustrated in FIG. 4(d). Therefore, a position of each of light sources used for two images is not very significant, and a position of a reflection image with glasses is determined depending on whether a plurality of light-emitting elements are located at substantially the same position as a whole.

Since the light-emitting elements 3A are adjacent to the light-emitting elements 3B, the light-emitting elements 3B can generate a reflection image with glasses having brightness, a size, and a shape to an extent capable of canceling or removing the reflection image with glasses by the light-emitting elements 3A using an image difference. Also, since the light-emitting elements 3C are arranged spaced apart from the light-emitting elements 3B on the outside of the aperture, when illumination light is emitted by the light-emitting elements 3C, reflected light from the pupil of the subject is reduced. Therefore, by picking up a light pupil image when illumination light is emitted by the light-emitting elements 3A, and picking up a dark pupil image when illumination light is emitted by the light-emitting elements 3B and 3C, it is possible to expand a difference in brightness between the light pupil image and the dark pupil image by the light-emitting elements 3A and the light-emitting elements 3C. At the same time, it is possible to equalize brightness and shapes of reflection image with glasses by the light-emitting elements 3A and the light-emitting elements 3B. As a result, it is possible to detect the pupil of the subject more conspicuously by taking a difference between the light pupil image and the dark pupil image which are picked up as described above.

Also, since the light-emitting elements 3C emit illumination light having a central wavelength of 950 nm, the illumination light emitted by the third light source is absorbed by a medium constituting an eyeball. Therefore, it is possible to reduce brightness of a pupil in the dark pupil image and easily detect the pupil of a subject.

In addition, since the light-emitting elements 3C are a pair of light sources arranged at symmetric positions with the aperture being interposed therebetween, balance of brightness of the face area of the subject is easily achieved in a case where illumination light is emitted by the light-emitting elements 3C. After a difference between a light pupil image and a dark pupil image is obtained, the difference is hardly left in a face portion of the subject. In this way, the pupil of the subject can be more precisely detected.

Figure 5:
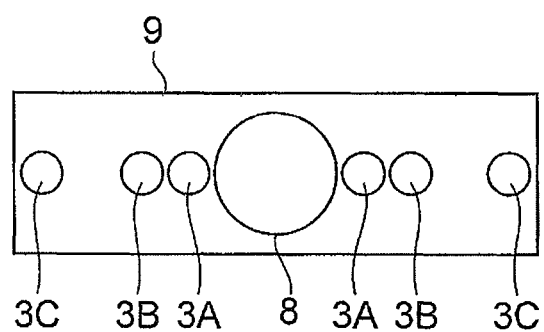
FIG. 5 is a diagram illustrating a modification example of the pupil detection light source device according to the first embodiment of the present invention.

Next, a modification example of the pupil detection light source device according to the first embodiment of the present invention will be described. FIG. 5 illustrates a modification example of the pupil device according to the first embodiment of the present invention. In the present modification example, a multichip LED in which a plurality of LED chips is mounted within a single package (a mold) is used as the light-emitting elements 3A, the light-emitting elements 3B, and the light-emitting elements 3C. Since the brightness of such a multichip LED is high, it is possible to reduce the number of the light-emitting elements 3A, the light-emitting elements 3B and the light-emitting elements 3C. Also, by particularly using a multichip LED as the light-emitting elements 3C, it is possible to make the reflection image with glasses small, making pupil detection easy. In the present modification example, two light-emitting elements 3A, two light-emitting elements 3B, two light-emitting elements 3C, and an aperture 8 are arranged on one straight line. The two light-emitting elements 3A are arranged such that the aperture 8 is interposed therebetween. The two light-emitting elements 3B are arranged such that the aperture 8 and the two light-emitting elements 3A are interposed therebetween. The two light-emitting elements 3C are arranged at positions spaced apart from the aperture 8, the light-emitting elements 3A, and the light-emitting elements 3B, such that the aperture 8, the light-emitting elements 3A, and the light-emitting elements 3B are interposed therebetween. Also, the numbers of the light-emitting elements 3A, the light-emitting elements 3B, and the light-emitting elements 3C are not limited to two, and can be set appropriately.

FIG. 6(a) illustrates a modification example of the pupil detection device according to the first embodiment of the present invention. In the present modification example, the light-emitting elements 3C are arranged to be spaced further apart from the light-emitting elements 3B. Also, FIG. 6(b) is a diagram illustrating a light emission timing of the light-emitting elements 3A, 3B, and 3C in the present modification example. The light emission timing of the present modification example is also the same as the pupil detection light source device according to the first embodiment.

Even in the pupil detection light source device of the present modification example, similarly to the light source 3 according to the first embodiment, a reflection image with glasses can be generated by the light-emitting elements 3B, the reflection image with glasses having brightness, a size, and a shape to an extent capable of canceling or removing the glasses-reflective image caused by the light-emitting elements 3A using an image difference, providing the same working effect as the light source according to the first embodiment. Also, according to the present modification example, since the light-emitting elements 3C are spaced apart from the light-emitting elements 3B and therefore, light is further reduced, which is incident on the pupil of the subject from the light-emitting elements 3C, is then reflected by the inside of the eyeball A of the subject, and is incident on a camera by passing through the pupil of the subject, the pupil of the subject is darkly reflected in the dark pupil image.

In addition, in the case of performing eye-gage detection of the subject, a cornea-reflected image generated by reflection of light from the light source 3 by a cornea of the subject is used as a reference point. Specifically, there is a method of preparing a plurality of light sources, obtaining a corneal sphere center by performing geometrical calculation based on positions of the light sources and a position of the cornea-reflected image, and obtaining a straight line connecting a three-dimensional image of a pupil and the corneal sphere center as a line-of-sight. In this case, since the light-emitting elements 3B and the light-emitting elements 3C can be sued as a plurality of light sources according to the present modification example, the present modification example is effective.

Also, in the present modification example, when the light-emitting elements 3C are disposed at symmetric positions with the aperture 8 being interposed therebetween, brightness distribution in a face of the subject in a case where the face surface of the subject is irradiated with illumination light by the light-emitting elements 3C is identical to brightness distribution in a case where the face surface of the subject is irradiated with illumination light by the light-emitting elements 3A, and it is possible to make it more easy to detect the pupil of the subject since a face portion of the subject is canceled by differential processing.

However, since it is necessary to cancel the face portion of the subject in a difference image by a difference between the light pupil image and the dark pupil image, and it is necessary to make a face brightness by the light-emitting elements 3B and the light-emitting elements 3C identical to a face brightness by the light-emitting elements 3A approximately, there is a need to weaken the light emission intensities of the light sources of the light-emitting elements 3B and the light-emitting elements 3C. Therefore, there is a case where the cornea-reflected image by the light-emitting elements 3B and 3C becomes dark and detection of the cornea-reflected image becomes difficult. In other cases, the following another modification example is effective.

Figure 7:
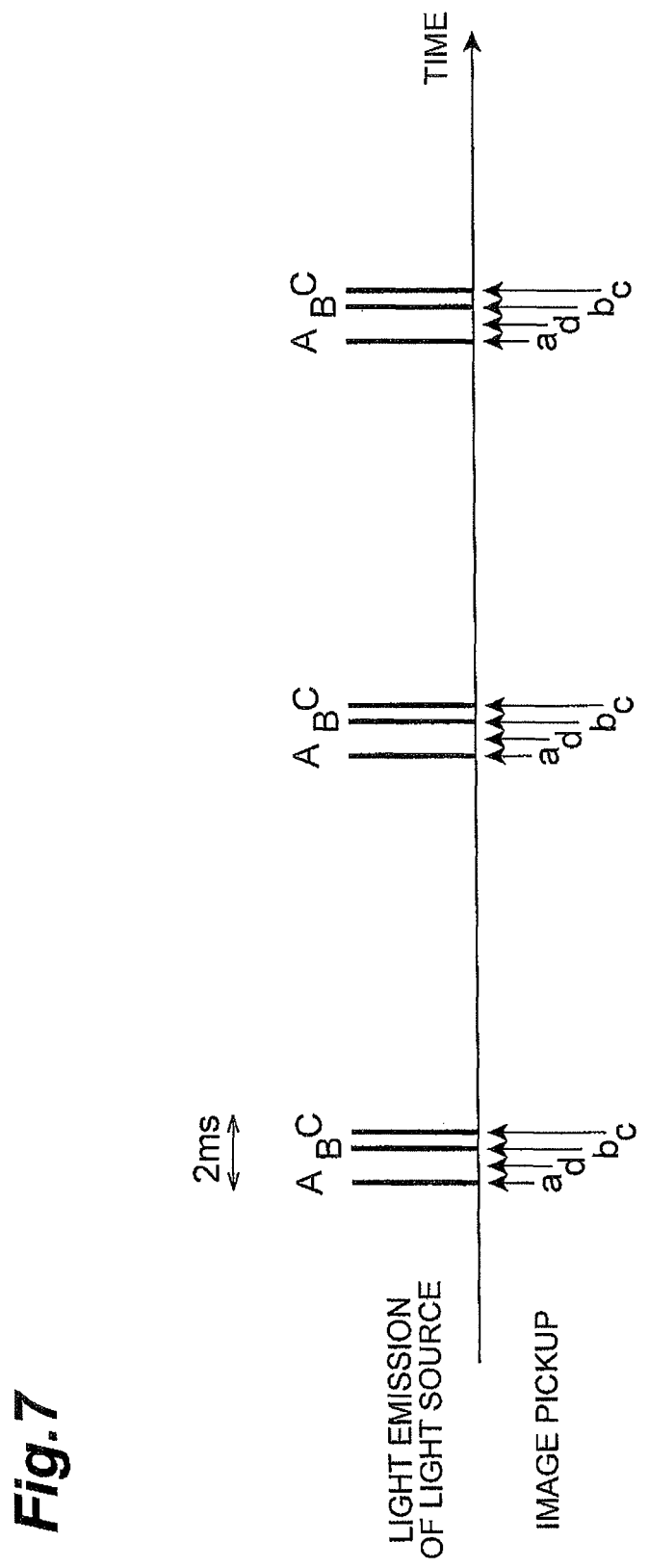
FIG. 7 is a diagram illustrating a light emission timing and an image timing of still another modification example of the pupil detection light source device according to the first embodiment of the present invention.
Figure 8:
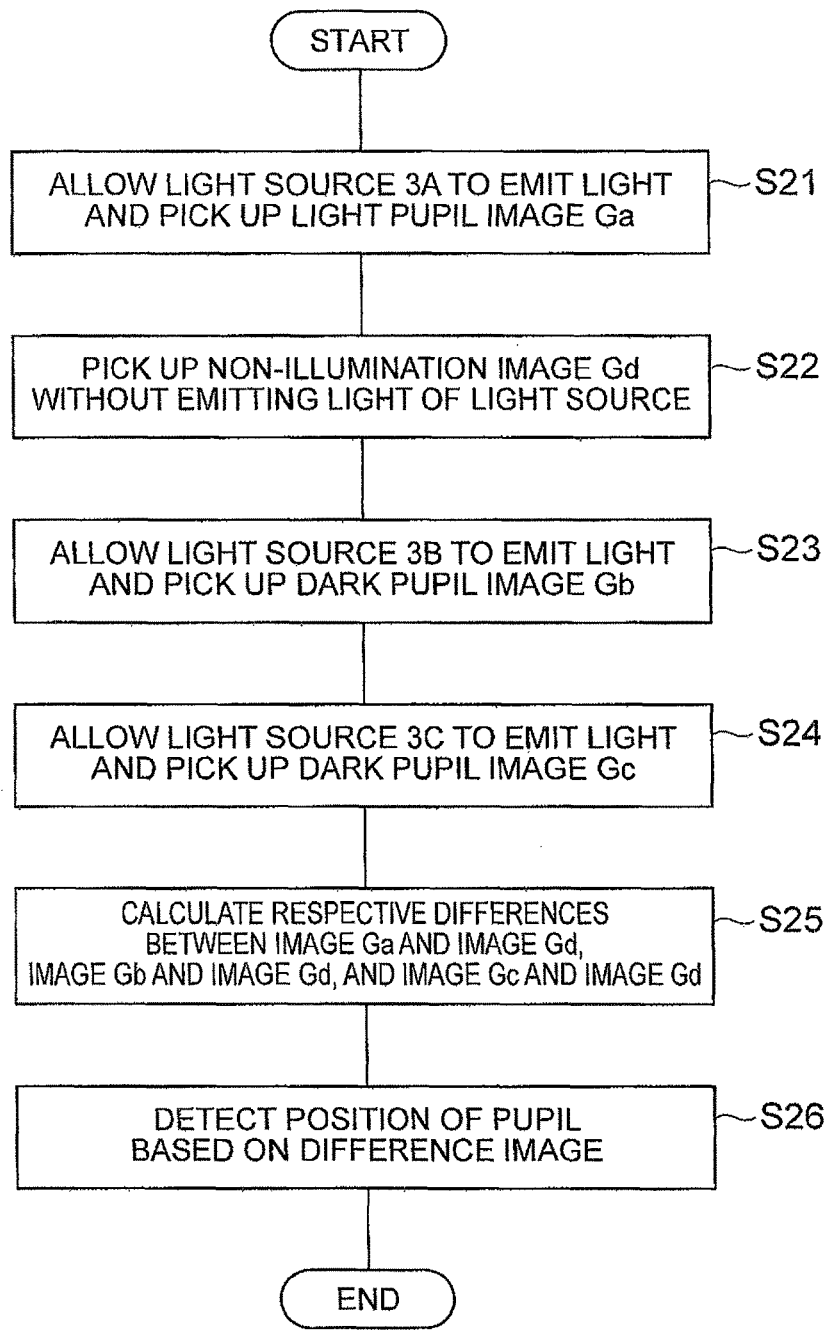
FIG. 8 is a flowchart of another modification example of the pupil detection method according to the first embodiment of the present invention.

FIG. 7 is a diagram illustrating a light emission timing and an image timing of another modification example of the pupil detection light source device according to the first embodiment, and FIG. 8 is a flowchart of a pupil detection method according to the modification example. In the present modification example, a high-speed camera capable of continuously capturing a frame image at short time intervals is used as the camera 2. As the camera 2 in the present modification example, any camera is possible as long as the camera is capable of capturing four frame images during, for example, two milliseconds.

Also, the control device 4 allows the light-emitting elements 3A to emit light at timing A of FIG. 7 and simultaneously, picks up a light pupil image Ga at timing indicated by arrow a, which is synchronized with the timing A of FIG. 7 (step S21). Next, the control device 4 picks up a non-illumination image Gd at timing indicated by arrow d, immediately after the timing A of FIG. 7 in a state where the light-emitting elements 3A, 3B, and 3C all are not lit (step S22). Next, the control device 4 allows the light-emitting elements 3B to emit light at timing B immediately after the timing indicated by the arrow d of FIG. 7 and simultaneously picks up a dark pupil image Gb at timing indicated by arrow b, which is synchronized with the timing B of FIG. 7 (step S23). Next, the control device 4 allows the light-emitting elements 3C to emit light at timing C immediately after the timing B of FIG. 7 and simultaneously picks up a dark pupil image Gc at timing indicated by arrow c, which is synchronized with the timing C of FIG. 7 (step S24). In addition, the control device 4 performs the steps S21 to S24 during a short time of, for example, about 2 milliseconds.

The control device 4 respectively calculates a difference between the light pupil image Ga and the non-illumination image Gd, a difference between the dark pupil image Gb and the non-illumination image Gd, and a difference between the dark pupil image Gc and the non-illumination image Gd (step S25). Finally, the control device 4 calculates a position of a pupil based on a difference image (step S26). Specifically, the control device 4 performs calculation by Formula $(pa-pd)/(k_1*(pb-pd)+k_2*(pc-pd))$ as image operation for pupil detection. That is, as disclosed in Japanese Patent Application Laid-Open No. 2008-246004, only a pupil portion of the subject is extracted by dividing a result obtained by subtracting an image in the case of turning off the light-emitting elements from the light pupil image by a result obtained by subtracting the image in the case of turning off the light-emitting elements from the dark pupil image. In addition, in the aforementioned Formula, pa is a pixel value of the light pupil image Ga, pb is a pixel value of the dark pupil image Gb, pc is a pixel value of the dark pupil image Gc, pd is a pixel value of the non-illumination image Gd, and $k_1$ and $k_2$ are adjustment values. Generally, since the pupil portion of the subject is represented by a pixel value larger than the face portion of the subject, it is possible to extract the pupil portion by binarization. $k_1$ and $k_2$ are set as coefficients for adjusting a pixel value in a case where one of, for example, the dark pupil image Gb and the dark pupil image Gc is too brighter or darker compared to the other. By calculating the difference between the light pupil image Ga and the non-illumination image Gd, the difference between the dark pupil image Gb and the non-illumination image Gd, and the difference between the dark pupil image Gc and the non-illumination image Gd, each image by only each light-emitting element is obtained, and influence of external light is removed. Simultaneously, a necessity to achieve balance of a light emission intensity of each light-emitting element is reduced, and convenience is obtained.

Also, as described above, no requirement of achievement of balance of light emission intensities of the light elements means that it is possible to make the brightness of the light-emitting elements 3B and the light-emitting elements 3C on a face image similar to that of the light-emitting elements 3A. This can make the brightness of the cornea-reflected image generated by the light-emitting elements 3B and the light-emitting elements 3C bright, thereby making cornea detection easy. Also, it is easy and preferable that cornea reflection necessary for point-of-sight detection is detected from a difference image between the light pupil image Ga and the non-illumination image Gd, a difference image between the dark pupil image Gb and the non-illumination image Gd, and a difference image between the dark pupil image Gc and the non-illumination image Gd.

In addition, since glass reflection is saturated in each of the light pupil image Ga, the dark pupil image Gb, and the dark pupil image Gc, when a pupil is detected by division as in the above Formula, a pixel value of glass reflection may exceed a pixel value of the pupil due to the balance of brightness of a face image by the light-emitting elements 3A, the light-emitting elements 3B, and the light-emitting elements 3C. The reason for this is as follows. In the case of increasing power of the light-emitting elements, the face portion or the pupil portion becomes bright in the light pupil image Ga, the dark pupil image Gb, and the dark pupil image Gc, in proportion to the increase. In contrast, since the glass reflection is saturated, it does not become brighter than a saturation value. As a result, as the power of the light-emitting elements increases, a pixel value of a glass reflected portion relatively decreases in images acquired by subtracting the non-illumination image Gd from the respective images. Therefore, in the case of division of the above Formula, when a term corresponding to a large image of light source power exists in a denominator, a pixel of glass reflection represents rather a large value than the pupil.

In this way, when the pixel value of glass reflection exceeds the pixel value of the pupil, the pupil cannot detected correctly and the glass reflection is detected as the pupil incorrectly. In order to prevent such erroneous detection, a binarized image in which a portion in which a pixel value is saturated is considered as the glass reflected portion (a pixel value of a glasses-reflected portions are zero, and pixel values of other portions are 1 (positive logic)) is generated with respect to each of the light pupil image Ga, the dark pupil image Gb, and the dark pupil image Gc, and a binary image (logical product image) obtained by taking a logical product of three binarized images is generated. The binary image includes all glasses-reflected portions of the light pupil image Ga, the dark pupil image Gb, and the dark pupil image Gc, and the pixel value of the glasses-reflected portions are zero and the pixel values of other portions are 1. By taking a logical product between the binary image and an image for pupil detection or an image for cornea reflection, it is possible to more certainly detect a pupil or cornea image from portions other than glass reflection.

As illustrated in FIG. 7, naturally, the aforementioned solution is applied similarly to problems related to the aforementioned glass reflection even in the case of lighting the light-emitting elements 3A at timing A and lighting the light-emitting elements 3B and the light-emitting elements 3C simultaneously at timing B.

Figure 9:
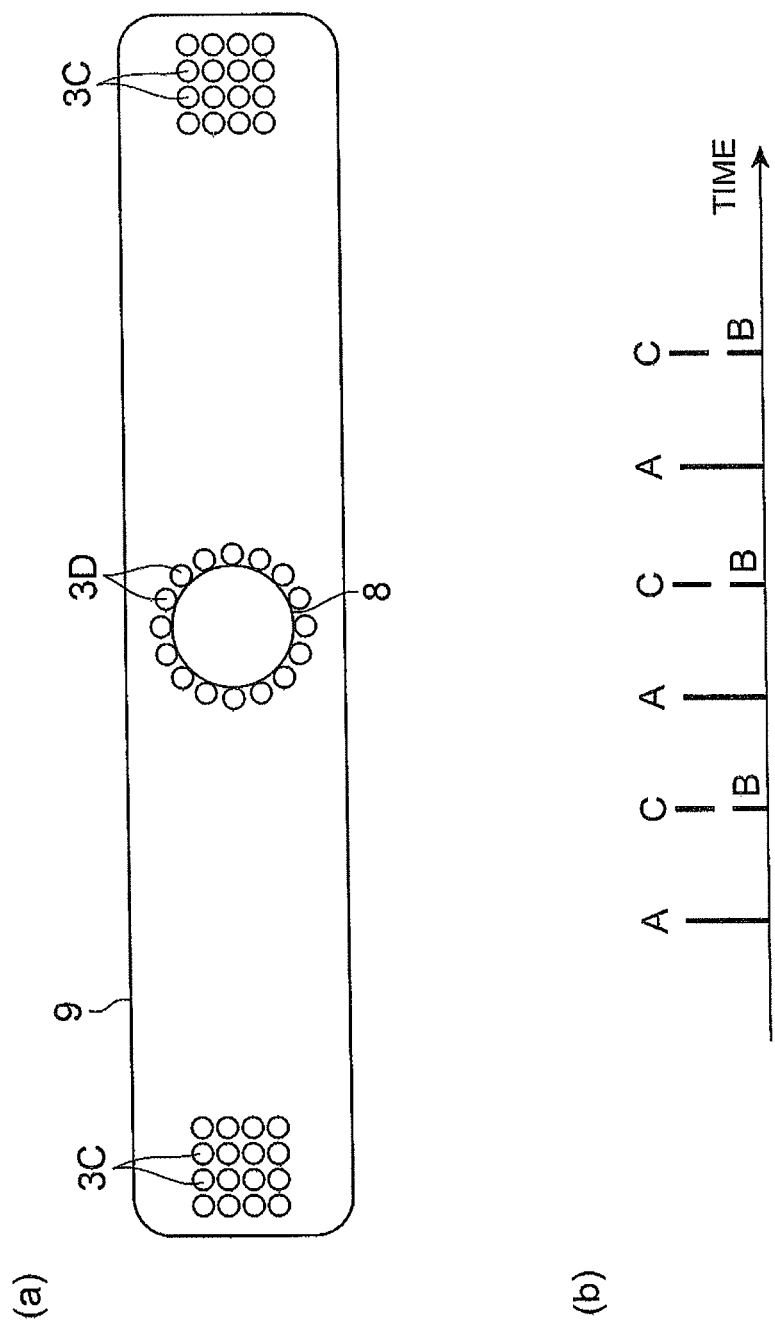
FIG. 9 is a diagram illustrating a configuration and a light emission timing of still another modification example of the pupil detection light source device according to the first embodiment of the present invention.

FIG. 9 is a diagram illustrating a configuration and a light emission timing of still another modification example of the pupil detection light source device according to the first embodiment. FIG. 9(a) illustrates a view of the light source 3 of FIG. 1 when seen from the outside of the housing 5. The pupil detection light source device illustrated in FIG. 9(a) includes light-emitting elements 3D, instead of the light-emitting elements 3A and 3B of the pupil detection light source device illustrated in FIG. 2(a). The light-emitting elements 3D include a plurality of LEDs in which a central wavelength of output light is 850 nm. In the present modification example, the light-emitting elements 3C include a plurality of LEDs in which a central wavelength of output light is 850 nm. the present modification example, the light-emitting elements 3D have both a function as a first light source and a function as a second light source.

FIG. 9(b) is a diagram illustrating a light emission timing of the light-emitting elements 3C and 3D in the present modification example. At timing A of FIG. 9(b), the light-emitting elements 3D are only allowed to emit light. In this case, the light-emitting element 3D functions as a first light source. At timing B of FIG. 9(b), the light-emitting elements 3D are allowed to emit light and, simultaneously, at timing C of FIG. 9(b), the light-emitting elements 3C are allowed to emit light. In this case, the light-emitting element 3D functions as a second light source. In this case, a light emission intensity of the light-emitting elements 3D at the timing B and C is weaker than a light emission intensity of the light-emitting elements 3D at the timing A. More specifically, the brightness in a face of a subject by the light-emitting elements 3D at the timing A is made approximately equal to brightness in the face of the subject by the light-emitting elements 3C and 3D at the timing B and C.

The present modification example provides the same working effect as the pupil detection light source device of the first embodiment. Also, in the present modification example, the light-emitting elements 3C and 3D which emit light at timing A, B, and C all have the same central wavelength of 850 nm. In this case, there are the following advantages compared to a case where one of the light-emitting elements 3C and 3D has a central wavelength of for example, 850 nm, and the other has another central wavelength of, for example, 950 nm. For example, in the case of using light-emitting elements having two different wavelengths of, for example, 850 nm and 950 nm as central wavelengths, it is necessary to capture light which is equivalently in a range of 800 nm to 1000 nm. Then, when there is strong external light having a wavelength of around 900 nm between, for example, 850 nm and 950 nm, the pupil detection device is adversely affected by the external light. In order to remove such adverse influence, it is necessary to prepare an optical filter that has two transmission peaks of 850 nm and 950 nm and blocks light having a wavelength of 900 nm. Therefore, such an optical filter is very expensive, and a thickness thereof is large, thereby making miniaturization of the pupil detection device difficult. On the other hand, as in the present modification example, when the central wavelengths of the light-emitting elements 3C and 3D are one wavelength of, for example, 850 nm, it is possible to use an optical filter having only one transmission peak of, for example, 850 nm Such an optical filter is relatively inexpensive. Further, since a peak width is made narrow due to use of one wavelength as central wavelengths of the light-emitting elements, it is possible to reduce influence of the aforementioned external light having a wavelength of 900 nm.

In addition, although the light-emitting elements 3A and 3B as described above are arranged adjacent to the aperture 8 and illumination light is emitted from the vicinity of the aperture 8, it may be possible to allow illumination light to be emitted from the inside of the aperture 8. As an example, it is possible to dispose a half mirror and the like at a position on the optical axis L of the objective lens 7 (see FIG. 1) and at the same time, dispose the light-emitting elements 3A and 3B at a position deviated from the optical axis L, within the camera 2. By disposing the light-emitting elements 3A and 3B and the half mirror, it is possible to reflect illumination light from the light-emitting elements 3A and 3B by the half mirror or the like, and irradiate toward a face of the subject with the illumination light from the inside of the aperture 8.

In addition, it may be possible to use a plurality of LEDs as the light-emitting elements 3A and 3B, dispose some of a plurality of LEDs as described above, and irradiate with the illumination light from the inside of the aperture 8. At the same time, it may be possible to dispose the others than the some of the plurality of LEDs adjacent to the aperture 8 and irradiate with the illumination light from the vicinity of the aperture 8. In this case, when seen from the subject, the light-emitting elements 3A and 3B irradiate with the illumination light from positions over both the inside and the vicinity of the aperture 8. However, even in this case, when seen from the subject, the light-emitting elements 3B needs to irradiate with the illumination light from a position at which a distance from a center of the aperture 8 is equal or larger in comparison to the light-emitting elements 3A.

(Second Embodiment)

Next, a pupil detection light source device, a pupil detection device, and a pupil detection method according to a second embodiment of the present invention will be described. In this embodiment, two cameras are disposed, a light pupil image and a dark pupil image are obtained by picking up an eyeball A of a subject by the two cameras respectively, and a pupil of the subject is detected based on the light pupil image and the dark pupil image obtained in respective coordinate systems of the two cameras. In addition, a three-dimensional position of the pupil is detected by performing stereo calibration on a pupil position of the subject obtained by the coordinate systems of the cameras, and a line-of-sight direction is detected by using the three-dimensional position of the pupil and a corneal reflection point separately detected. A configuration of the pupil detection device of the present embodiment is similar to that of the pupil detection device of the first embodiment illustrated in FIG. 1, except for arrangement of the light-emitting elements and the aperture in the light source 3.

Figure 10:
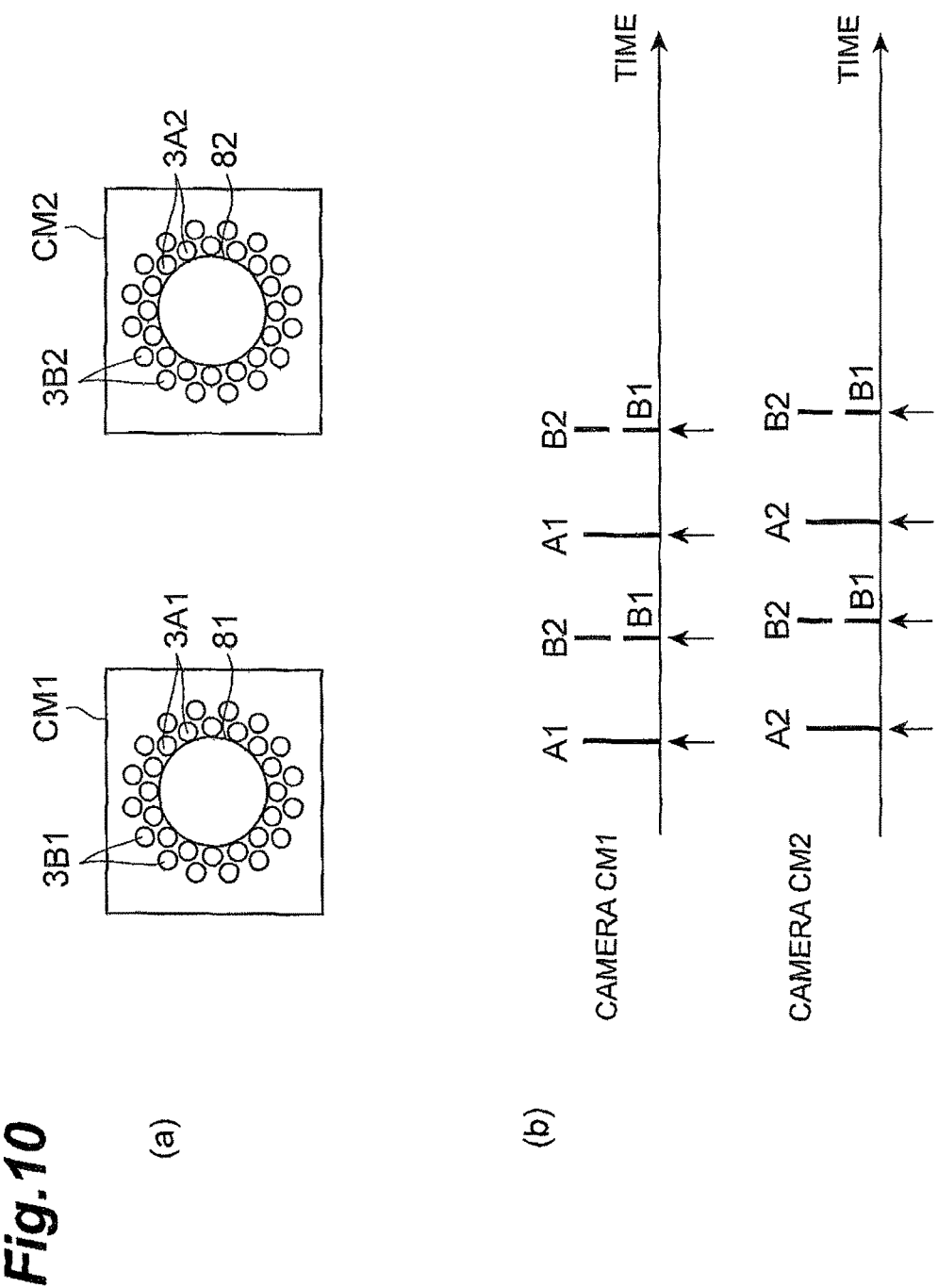
FIG. 10 is a diagram illustrating a configuration and a light emission timing of a pupil detection light source device according to a second embodiment of the present invention.

FIG. 10(a) is a plan view of a pupil detection light source device according to the second embodiment when seen from the outside of the housing 5. In the pupil detection light source device, an aperture 81 (first aperture) and an aperture 82 (second aperture) corresponding to the two cameras are provided. Light-emitting elements 3A1 (first light source) and light-emitting elements 3A2 (fourth light source) include a plurality of LEDs in which a central wavelength of output light is 850 nm (first central wavelength). The light-emitting elements 3A1 are arranged in a ring shape at equal intervals along edges of the aperture 81 on the outside of the aperture 81. The light-emitting elements 3A2 are arranged in a ring shape at equal intervals along edges of the aperture 81 on the outside of the aperture 82.

The light-emitting elements 3B1 (second light source) include a plurality of LEDs in which a central wavelength of output light is 950 nm (second central wavelength) and are arranged in a ring shape at equal intervals adjacent to the outsides of the light-emitting elements 3A1. The light-emitting elements 3B2 (third light source) include a plurality of LEDs in which a central wavelength of output light is 950 nm and are arranged in a ring shape at equal intervals adjacent to the outsides of the light-emitting elements 3A2. In addition, when seen from the subject, a camera CM1 (first camera) is disposed at a depth part of the aperture 81 and a camera CM2 (second camera) is disposed at a depth part of the aperture 82.

Figure 11:
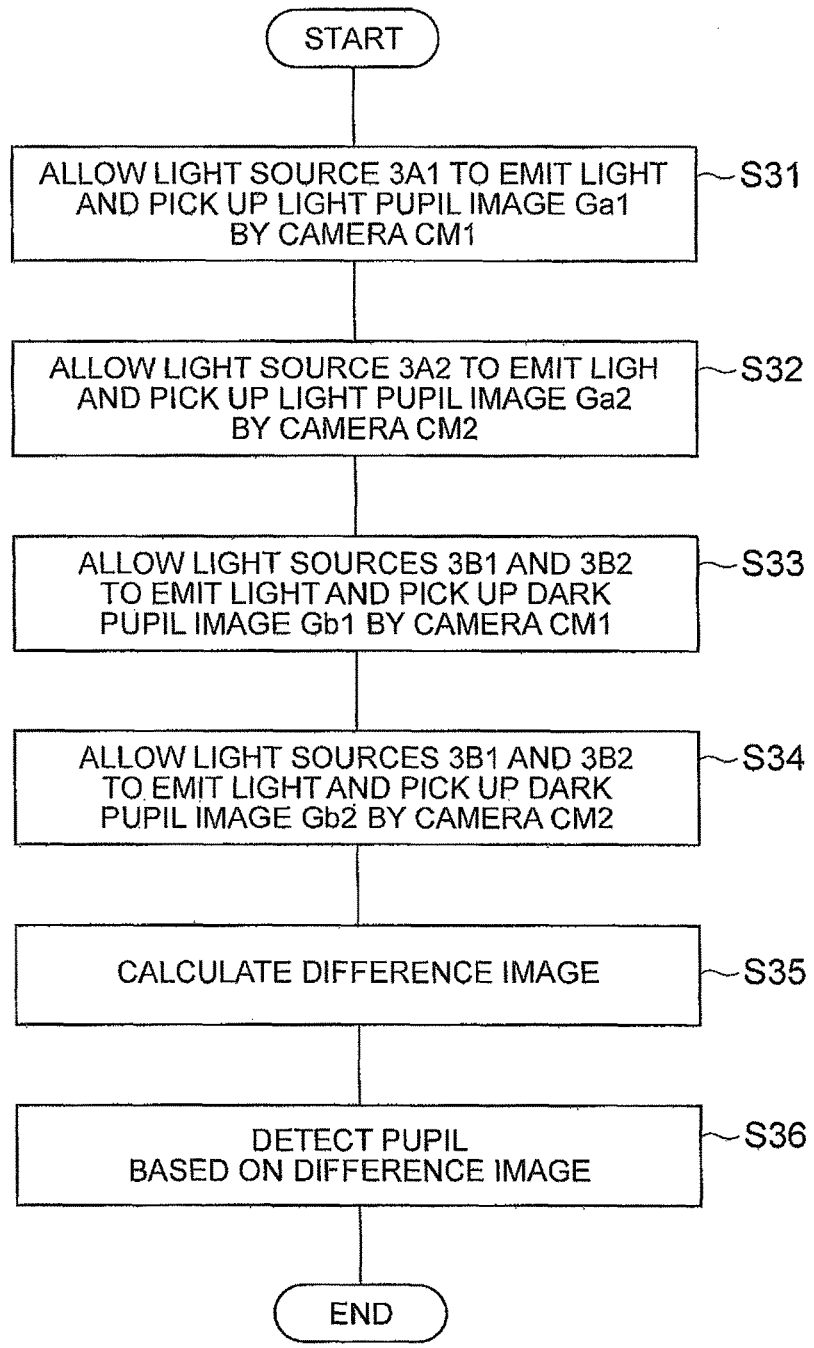
FIG. 11 is a flowchart of a pupil detection method according to a second embodiment of the present invention.

FIG. 10(b) is a diagram illustrating a light emission timing and an image timing of the pupil detection light source device, and FIG. 11 is a flowchart of a pupil detection method using the pupil detection light source device. Also, the control device 4 allows the light-emitting elements 3A1 to emit light and simultaneously picks up a light pupil image Ga1 by using the camera CM1 (step S31). Subsequently, the control device 4 allows the light-emitting elements 3A2 to emit light and simultaneously picks up a light pupil image Ga2 by using the camera CM2 (step S32). Also, in order to prevent crosstalk of light from occurring between the cameras CM1 and CM2, the control device 4 shifts timing at which the steps S31 and S32 are performed.

Next, the control device 4 allows the light-emitting elements 3B1 and 3B2 to emit light and simultaneously picks up a dark pupil image Gb1 by using the camera CM1 (step S33). Subsequently, the control device 4 allows the light-emitting elements 3B1 and 3B2 to emit light and simultaneously picks up a dark pupil image Gb2 by using the camera CM2 (step S34).

Then, the control device 4 calculates a difference image between the light pupil image Ga1 and the dark pupil image Gb1 and a difference image between the light pupil image Ga2 and the dark pupil image Gb2 (step S35). The control device 4 detects a pupil of the subject based on the difference image (step S36). Thereafter, the pupil detection device 1 repeatedly performs the aforementioned steps S31 to S36 at a constant period.

According to the pupil detection light source device of the second embodiment as described above, in the case of calculating a three-dimensional coordinate of the pupil of the subject to perform line-of-sight detection by performing stereo calibration on the pupil position detected by using the two cameras CM1 and CM2, it is possible to use the light-emitting elements 3B1 and 3B2 for both image of the cameras CM1 and CM2, and further miniaturize the pupil detection light source device due to no requirement of an extra space in which the light-emitting elements are disposed.

FIG. 12(a) illustrates a pupil detection light source device according to a modification example of the second embodiment. The present modification example differs from the aforementioned pupil detection light source device according to the second embodiment in that the pupil detection light source device of the present modification example further includes light-emitting elements 3C1 (fifth light source) and light-emitting elements 3C2 (sixth light source). The light-emitting elements 3C1 are arranged at symmetric positions to the light-emitting elements 3B2 with the aperture 81 being interposed therebetween, and emits illumination light having a central wavelength of 950 nm toward the subject. The light-emitting elements 3C2 are arranged at symmetric positions to the light-emitting elements 3B1 with the aperture 82 being interposed therebetween, and emits illumination light having a central wavelength of 950 nm toward the subject.

Figure 12:
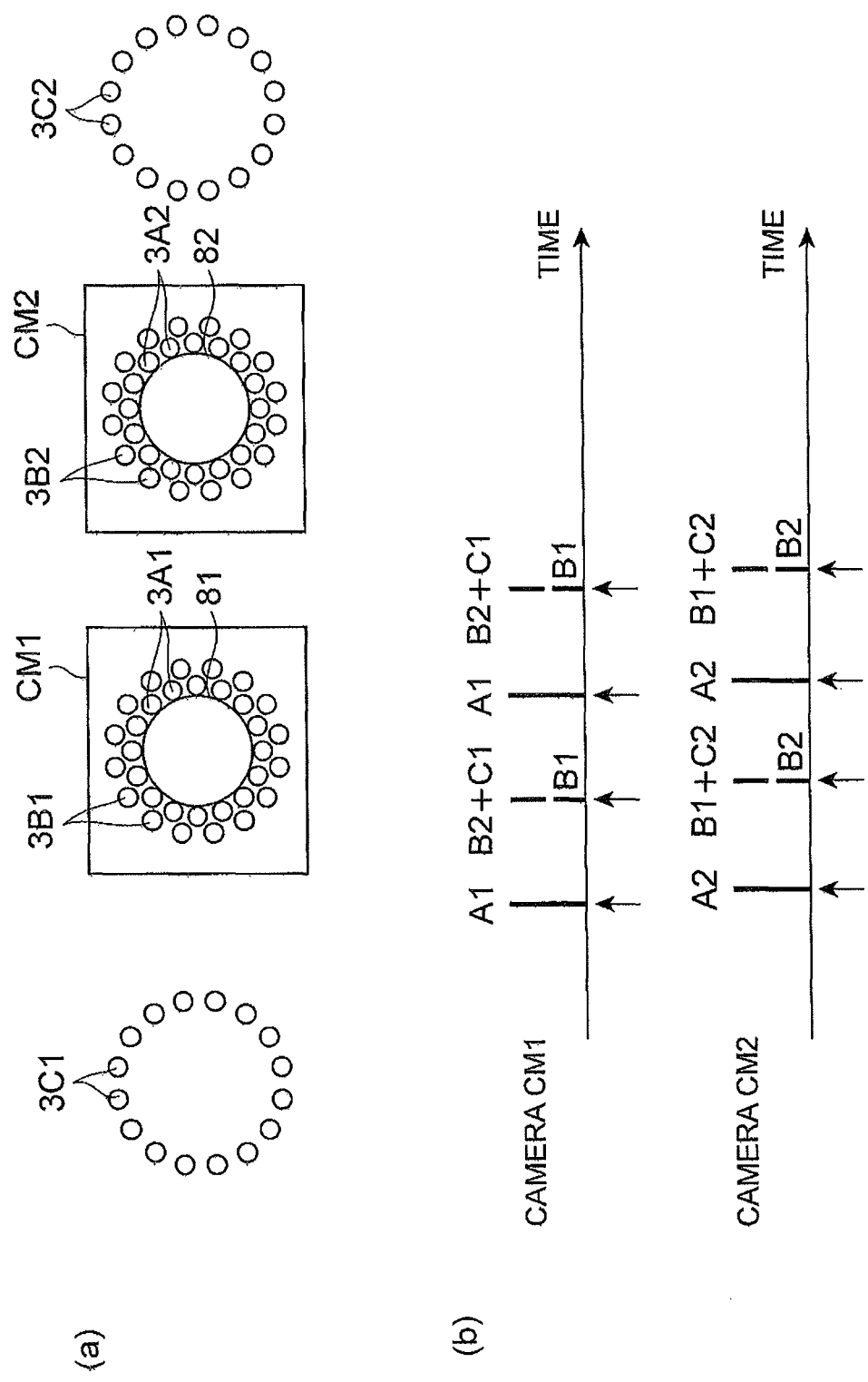
FIG. 12 is a diagram illustrating a light emission timing and an image timing of a pupil detection light source device according to another modification example of the second embodiment of the present invention.

FIG. 12(*b*) illustrates a light emission timing of the pupil detection light source device according to the present modification example. Also, the control device 4 allows the light-emitting elements 3A1 to emit light and picks up a light pupil image of the subject by the camera CM1. Subsequently, the control device 4 allows the light-emitting elements 3A2 to emit light and picks up a light pupil image of the subject by the camera CM2. Thereafter, the control device 4 allows the light-emitting elements 3B1, 3B2, and 3C1 to emit light and picks up a dark pupil image of the subject by the camera CM1. Then, the control device 4 allows the light-emitting elements 3B1, 3B2, and 3C2 to emit light and picks up a dark pupil image of the subject by the camera CM2. In this case, in order to prevent crosstalk of light, the control device 4 shifts image timing of the camera CM1 and the camera CM2.

According to the aforementioned pupil detection light source device of the modification example, when illumination light is emitted by the light-emitting elements 3B2 and the light-emitting elements 3C1 arranged at symmetric positions with the aperture 81 being interposed therebetween, the dark pupil image is picked up by the camera CM1 through the aperture 81, and when illumination light is emitted by the light-emitting elements 3B1 and the light-emitting elements 3C2 arranged at symmetric positions with the aperture 82 being interposed therebetween, the dark pupil image is picked up by the camera CM2 through the aperture 82. In this way, it is possible to achieve balance of brightness of the face of the subject in the picked-up dark pupil image and remove a face portion of the subject by differential processing, making pupil detection easier.

Also, the central wavelength of the illumination light emitted by the light-emitting elements 3C1 and the light-emitting elements 3C2 may not be necessarily 950 nm and may be 850 nm which is identical to the central wavelength of the illumination light emitted by, for example, the light-emitting elements 3A1 and the light-emitting elements 3A2. Also, in FIG. 12(*b*), at timing at which the light-emitting elements 3B1, 3B2, and 3C1 are allowed to emit light, instead of the light-emitting elements, the light-emitting elements 3A2, 3C1, and 3B1 may be allowed to emit light. At timing at which the light-emitting elements 3B1, 3B2, and 3C2 are allowed to emit light, instead of the light-emitting elements, the light-emitting elements 3A1, 3C2, and 3B2 may be allowed to emit light. Also, the light-emitting elements 3C1 and 3C2 illustrated in FIG. 12(*a*) may be integrated LEDs of very high brightness, not LEDs arranged in a ring shape, and may be general LEDs arranged in a square shape.

FIG. 13(*a*) illustrates a pupil detection light source device according to another modification example of the second embodiment. Although the pupil detection light source device of the present modification example includes two apertures 81 (first aperture) and 82 (second aperture) like the pupil detection light source device of the second embodiment, arrangement of the light-emitting elements is different as described below.

The light-emitting elements 3A5 (first light source) include a plurality of LEDs in which a central wavelength of output light is 850 nm and are arranged in a ring shape at equal intervals along edges of the aperture 81 on the outside of the aperture 81. The light-emitting elements 3A6 (fourth light source) include a plurality of LEDs in which a central wavelength of output light is 850 nm and are arranged in a ring shape at equal intervals along edges of the aperture 82 on the outside of the aperture 82. In addition, the light-emitting elements 3B5 (second light source) include a plurality of LEDs in which a central wavelength of output light is 950 nm and are arranged adjacent to the outsides of the light-emitting elements 3A5. The emission elements 3B6 (fifth light source) include a plurality of LEDs in which a central wavelength of output light is 950 nm and are arranged adjacent to the outsides of the light-emitting elements 3A6.

In addition, light-emitting elements 3C5 (third light source) are arranged in the opposite side of the aperture 82 when seen from the aperture 81. The light-emitting elements 3C5 are spaced apart from the light-emitting elements 3B5 on the outside of the aperture 81. Also, light-emitting elements 3C6 (seventh light source) are arranged in the opposite side of the aperture 81 when seen from the aperture 82. The light-emitting elements 3C6 are spaced apart from the light-emitting elements 3B6 on the outside of the aperture 82. Also, the light-emitting elements 3C7 (sixth light source) are arranged between the aperture 81 and the aperture 82, in a state where a position at which a distance from the aperture 81 and a distance from the aperture 82 are made equal to each other is set as a center. The light-emitting elements 3C5 are arranged at point-symmetric positions to the light-emitting elements 3C7 with the aperture 81 being interposed therebetween, and the light-emitting elements 3C6 are arranged at point-symmetric positions to the light-emitting elements 3C3 with the aperture 82 being interposed therebetween. The light-emitting elements 3C5, 3C6, and 3C7 include a plurality of LEDs in which a central wavelength of output light is 950 nm and are arranged in a ring shape at equal intervals like the light-emitting elements 3B5 and 3B6.

FIG. 13(*b*) illustrates a light emission timing of the pupil detection light source device of the present modification example. Also, the control device 4 allows the light-emitting elements 3A5 to emit light and simultaneously picks up an image of the subject by the camera CM1. Subsequently, the control device 4 allows the light-emitting elements 3A6 to emit light and simultaneously picks up an image of the subject by the camera CM2. Thereafter, the control device 4 allows the light-emitting elements 3B5, 3C5, and 3C7 to emit light and simultaneously picks up an image of the subject by the camera CM1. Thereafter, the control device 4 allows the light-emitting elements 3B6, 3C6, and 3C7 to emit light at the same time and simultaneously picks up an image of the subject by the camera CM2.

According to the pupil detection light source device of the another modification example, when illumination light is emitted by the light-emitting elements 3C5 and the light-emitting elements 3C7 arranged at symmetric positions with the aperture 81 being interposed therebetween, the dark pupil image is picked up by the camera CM1 through the aperture 81, and when illumination light is emitted by the light-emitting elements 3C6 and the light-emitting elements 3C7 arranged at symmetric positions with the aperture 82 being interposed therebetween, the dark pupil image is picked up by the camera CM2 through the aperture 82. In this way, it is possible to achieve balance of brightness of the face of the subject in the dark pupil image and remove a face portion of the subject by differential processing, making pupil detection easier. In addition, it is possible to further miniaturize the pupil detection light source device since the light-emitting elements 3C7 can be used in common at the time of image by the camera CM1 and at the time of image by the camera CM2.

Figure 14:
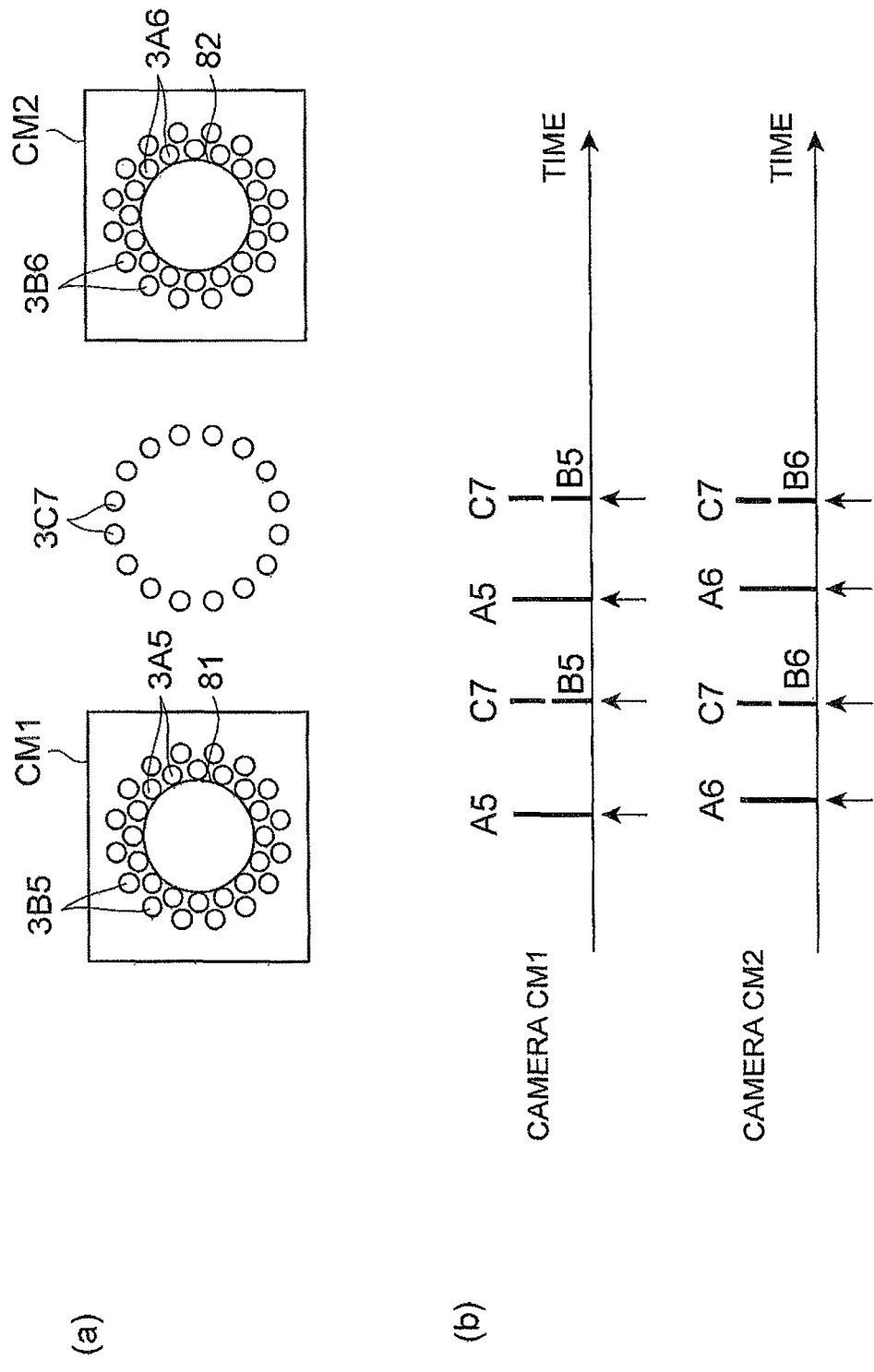
FIG. 14 is a diagram illustrating a light emission timing and an image timing of a pupil detection light source device according to still another modification example of the second embodiment of the present invention.

In addition, as illustrated in FIG. 14, the light-emitting elements 3C5 and the light-emitting elements 3C6 can be omitted in the pupil detection light source device illustrated in FIG. 13(a).

Figure 15:
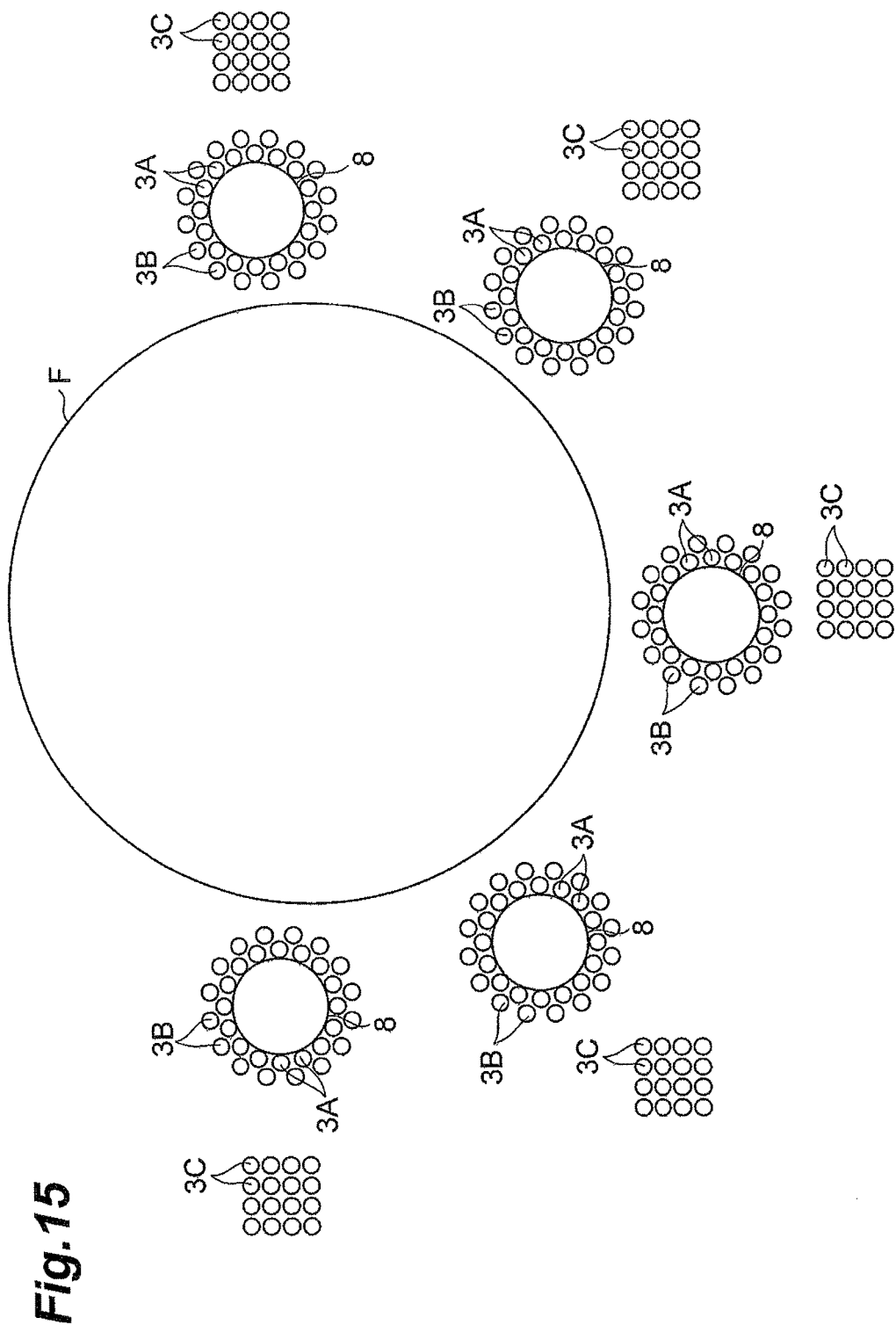
FIG. 15 is a diagram schematically illustrating arrangement of light sources in a pupil detection light source device according to a modification example of the present invention.

Further, the present invention is not limited to the aforementioned embodiments. For example, as illustrated in FIG. 15, it is preferable that attachment positions of the light-emitting elements 3C are arranged in a direction away from a center of a visual field F of the subject, that is, in a direction away from a range toward which the subject's sight is directed with respect to the light-emitting elements 3B when seen from the subject. When the light-emitting elements 3C are arranged as described above, a reflection image with glasses of the subject is difficult to overlap a pupil of the subject in an image captured by a camera, and the pupil of the subject is easily detected without being affected by the reflection image with glasses.

Figure 16:
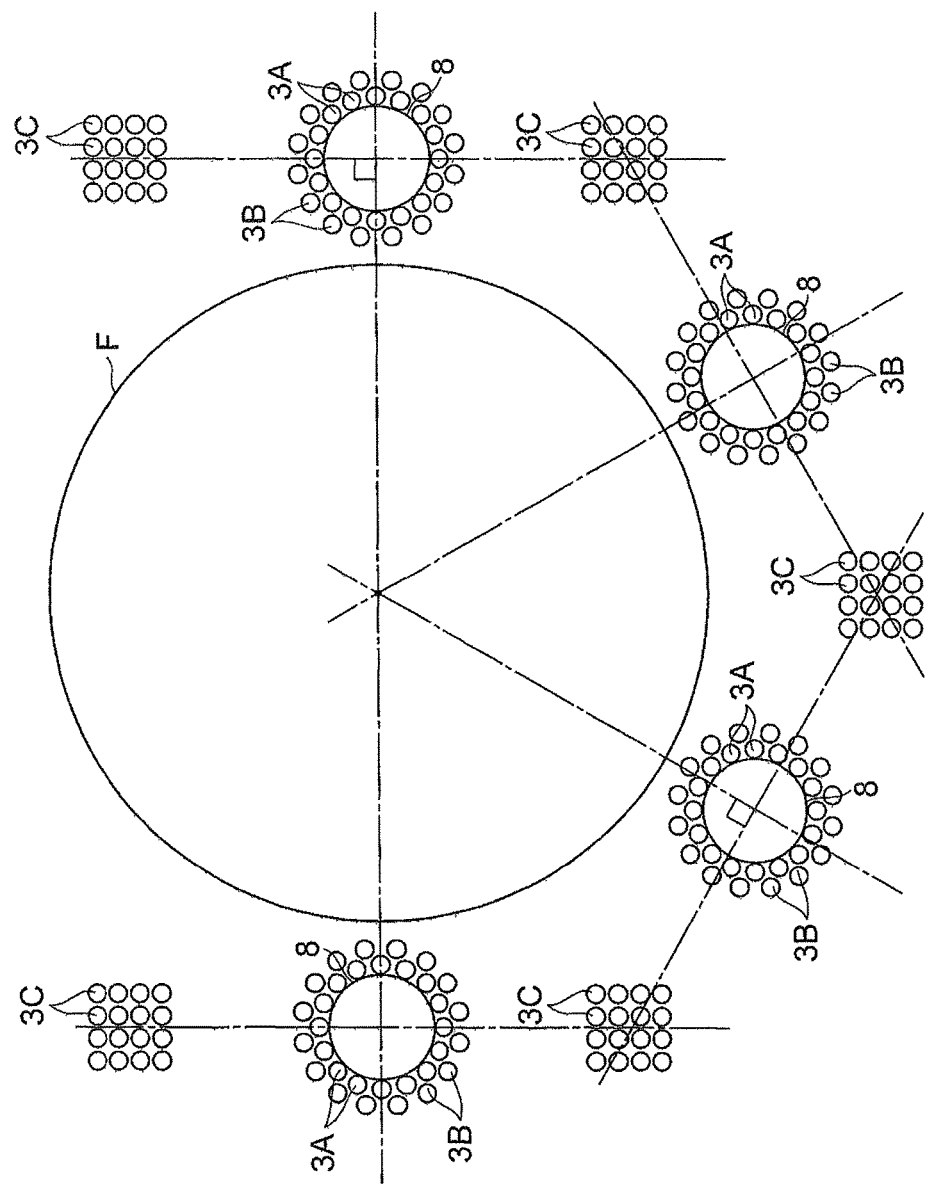
FIG. 16 is a diagram schematically illustrating arrangement of light sources in a pupil detection light source device according to another modification example of the present invention.

Also, as illustrated in FIG. 16, a plurality of cameras (for example, four in FIG. 16) and a plurality of pairs of light-emitting elements 3C (for example, five pairs in FIG. 16) may be arranged alternately at equal intervals in a range of the visual field F of the subject, and adjacent light-emitting elements 3C may be arranged at symmetric positions with respect to an axis connecting the center of the visual field F of the subject and a center of an aperture 8 of the camera.

Figure 6:
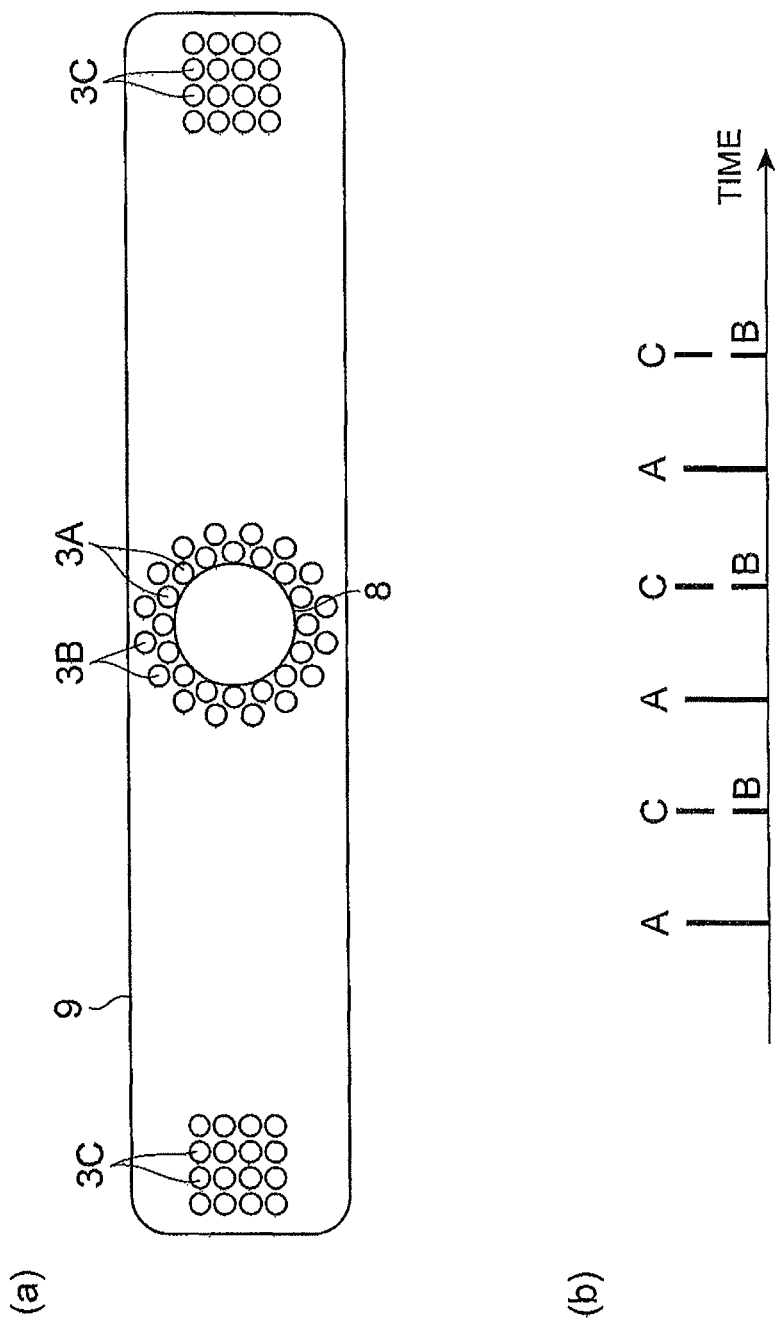
FIG. 6 is a diagram illustrating a configuration and a light emission timing of another modification example of the pupil detection light source device according to the first embodiment of the present invention.

Also, when small light sources, for example, LEDs are used as the light-emitting elements 3A and the light-emitting elements 3B in FIGS. 2, 6 and 15, light-emitting elements 3A and light-emitting elements 3B may be distributed in at a ratio of necessary numbers as follows. For example, when the light-emitting elements 3A and the light-emitting elements 3B are arranged at a ratio of 1:2, three light-emitting elements of the light-emitting element 3A, the light-emitting element 3B, and the light-emitting element 3B are set as one set, and the set is arranged in the vicinity of the aperture sequentially, in a line along the circumference of the aperture 8 of the camera. Also, when the light-emitting elements 3A and the light-emitting elements 3B need to have more large power because of bright surroundings or the like, the light-emitting elements 3A and the light-emitting elements 3B are arranged similarly in second and subsequent lines, so as to be as close as possible to the vicinity of the aforementioned line of light-emitting elements arranged in a line. Also, the light-emitting elements 3A are arranged in the closest line to the aperture 8, and the light-emitting elements 3B are arranged in two lines so as to be adjacent to the vicinity thereof In the case of requiring large power, the light-emitting elements 3A are arranged in two lines closest to the aperture 8, and the light-emitting elements 3B are arranged in four lines so as to be adjacent to the vicinity thereof Also, the light-emitting element 3A, the light-emitting element 3B, the light-emitting element 3B, the light-emitting element 3A, the light-emitting element 3B, and the light-emitting element 3B may be arranged by one line in the order thereof from near the aperture 8. When a reflection image with glasses of the light-emitting element 3A and the light-emitting element 3B are offset from each other, arrangement may be made in the order of the light-emitting element 3A, the light-emitting element 3B, the light-emitting element 3A, the light-emitting element 3B, the light-emitting element 3A, and the light-emitting element 3B.

Also, in a case where a first camera and a second camera are prepared at a depth part of the aperture 8 when seen from the subject in the pupil detection light source device 3 illustrated in FIG. 2, the pupil detection device can be configured as follows.

The central wavelength of the light-emitting element 3A is set to 850 nm (first central wavelength). The central wavelengths of the light-emitting elements 3B and 3C is set to 950 nm (second central wavelength). For example, wavelength separating unit, such as a half mirror or a dichroic mirror, is provided inside the aperture 8 when seen from the subject. The wavelength separating unit performs wavelength separation on light reaching the wavelength separating unit by passing through the aperture from the subject, and allows light of around a wavelength of 850 nm to be incident on the first camera and allows light of around a wavelength of 950 nm to be incident on the second camera. In addition, the control device 4 allows the light-emitting elements 3A, and the light-emitting elements 3B and 3C to emit light simultaneously. Therefore, it is possible to capture a light pupil image made of light of around a wavelength of 850 nm by the first camera, and capture a dark pupil image made of light of around a wavelength of 950 nm by the second camera.

Also, although an LED is used as a light-emitting element in the aforementioned embodiments, a certain surface light emitting body having directionality may be used instead of the LED. Also, a detection target by the pupil detection light source device, the pupil detection device, and the pupil detection method of the present invention is not limited to a pupil of a person and may detect an artificial pupil attached to a robot or the like, which has a shape imitating, for example, the pupil of a person, as the detection target.

Also, it is also possible to perform pupil detection by using the pupil detection light source device of the present invention and a rolling shutter type image sensor. For example, there has been known a pupil detection device and a pupil detection method, which obtain light pupil image data and dark pupil image data for each of alternate lines of the rolling shutter type image sensor and detect a pupil by obtaining a difference between the light pupil image data and dark pupil image data as in Japanese Patent No. 4528976. When the pupil detection light source device of the present invention is applied to the pupil detection device and the pupil detection method, a face of a subject may be irradiated with first light sources (for example, light-emitting elements 3A illustrated in FIG. 2) at timing at which, for example, the light pupil image is obtained and the face of the subject may be irradiated with second light sources (for example, light-emitting elements 3B illustrated in FIG. 2) and third light sources (for example, light-emitting elements 3C illustrated in FIG. 2) at timing at which, for example, the dark pupil image is obtained.

In the pupil detection light source device of the present embodiment, the second light sources may emit illumination light having a central wavelength which allows the brightness of the pupil of the subject in a dark pupil image to be relatively darker than the brightness of the pupil of the subject in a light pupil image. In this case, since the brightness of the pupil of the subject in the dark pupil image is relatively darker than the brightness of the pupil of the subject in the light pupil image, it is possible to detect the pupil of the subject more conspicuously by obtaining a difference between the light pupil image and the dark pupil image.

Also, the illumination light emitted by the first light sources has a first central wavelength, and the illumination light emitted by the second light sources has a second central wavelength longer than the first central wavelength. Generally, light having a short wavelength is less absorbed by a medium constituting an eyeball, compared to light having a long wavelength. Therefore, the illumination light for obtaining the dark pupil image, which is emitted by the second light sources is less reflected from the inside of the pupil of the subject, compared to the illumination light for obtaining the bright pupil, which is emitted by the first light sources. In this case, the brightness of the pupil of the subject in the dark pupil image is darker than the brightness of the pupil of the subject in the light pupil image, and the difference between the light pupil image and the dark pupil image is obtained, making it possible to detect the pupil of the subject more conspicuously.

In this case, the third light source may emit illumination light having the second central wavelength. In this case, since the illumination light emitted by the third light source is absorbed by the medium constituting the eyeball, it is possible to reduce the brightness of the pupil in the dark pupil image and detect the pupil of the subject more easily.

Also, the third light source may be at least a pair of light sources arranged at symmetric positions with the aperture being interposed therebetween. In this case, balance of brightness of the face of the subject in a case where the illumination light is emitted by the third light source is easily achieved, and the difference is hardly left in a face portion of the subject after the difference between the light pupil image and the dark pupil image is taken. In this way, the pupil of the subject can be more precisely detected.

Also, the third light source may be arranged in a direction away from a center of a visual field of the subject with respect to the second light source when seen from the subject. In this case, since the third light source may be arranged in the direction away from the center of the visual field of the subject, a reflection image with glasses and the pupil of the subject do not overlap each other when seen from the aperture and it is possible to reduce reverse influence of glass reflection in the case of detecting the pupil of the subject.

Also, in a case where the aforementioned camera is set as a first camera, and an aperture provided in the first camera is set as a first aperture, a second aperture and a fourth light source may be included, the second aperture being an aperture disposed to face the subject to allow light from the pupil of the subject to pass therethrough and provided in a second camera, and the fourth light source irradiating illumination light for obtaining the light pupil image by the second camera toward a face of the subject from at least one of the inside or the vicinity of the second aperture when seen from the subject. The third light source may irradiate toward the face of the subject with illumination light from a position which exists in at least one of the inside or the vicinity of the second aperture when seen from the subject, and at which a distance from a center of the second aperture is equal or large in comparison to a position of the fourth light source. In this case, in order to image an image of the face of the subject through the first aperture using the first camera and image a picture of the face of the subject through the second aperture using the second camera, it is possible to allow the first camera to image the light pupil image when illumination light is emitted by the first light source, allow the second camera to image the light pupil image when illumination light is emitted by the fourth light source, and allow each of the first camera and the second camera to image the dark pupil image when the illumination light is emitted by the second light source and the third light source. Therefore, in the case of detecting a line-of-sight by calculating a three-dimensional coordinate of the pupil of the subject by using two cameras, it is possible to use the second light source and the third light source for image of both the first camera and the second camera, thereby not requiring an extra space in which the light sources are disposed and further miniaturizing the pupil detection light source device. Also, the pupil detection light source device can be used in the case of not performing stereo calibration on two cameras as described in Japanese Patent No. 4491604.

Also, a fifth light source and a sixth light source may be further included, the fifth light source irradiating illumination light for obtaining a dark pupil image by the first camera from a symmetric position to the third light source with the first aperture being interposed therebetween, and the sixth light source irradiating illumination light for obtaining a dark pupil image by the second camera from a symmetric position to the second light source with the second aperture being interposed therebetween. In this case, by picking up the dark pupil image by the first camera through the first aperture when illumination light is emitted by the third light source and the fifth light source arranged at symmetric positions with the first aperture being interposed therebetween, and picking up the dark pupil image by the second camera through the second aperture when illumination light is emitted by the second light source and the sixth light source arranged at symmetric positions with the second aperture being interposed therebetween, it is possible to achieve balance of brightness of the face of the subject in the picked-up dark pupil image and remove the face portion of the subject through differential processing making pupil detection more easier.

Also, in a case where the aforementioned camera is set as a first camera, and an aperture provided in the first camera is set as a first aperture, a second aperture, a fourth light source, a fifth light source, a sixth light source, and a seventh light source may be included. The second aperture is an aperture disposed to face the subject to allow light from the pupil of the subject to pass therethrough and provided in a second camera, and the fourth light source irradiates illumination light for obtaining the light pupil image by the second camera toward a face of the subject. The fifth light source irradiates illumination light for forming a reflection image with glasses to an extent capable of canceling the reflection image with glasses of the subject in the light pupil image obtained by the second camera by using an image difference, toward the subject from a position which exists in at least one of the inside or the vicinity of the second aperture when seen from the subject, and at which a distance from a center of the second aperture is equal or large in comparison to a position of the fourth light source. The sixth light source irradiates illumination light for obtaining the dark pupil image by the first camera and the second camera toward the face of the subject from a position at which a distance from the first aperture is equal to a distance from the second aperture between the first aperture and the second aperture, and the seventh light source irradiates illumination light for obtaining the dark pupil image by the second camera toward the face of the subject from a symmetric position to the sixth light source with the second aperture being interposed therebetween, which is a position spaced apart from the second aperture when seen from the subject. The third light source may irradiate illumination light from a symmetric position to the seventh light source with the first aperture being interposed therebetween. In this case, by picking up the dark pupil image by the first camera through the first aperture when illumination light is emitted by the third light source and the sixth light source arranged at symmetric positions with the first aperture being interposed therebetween, and picking up the dark pupil image by the second camera through the second aperture when illumination light is emitted by the sixth light source and the seventh light source arranged at symmetric positions with the second aperture being interposed therebetween, it is possible to achieve balance of brightness of the face of the subject in the dark pupil image and remove the face portion of the subject through differential processing making pupil detection more easier and, at the same time, further miniaturize the pupil detection light source device since the sixth light source can be used in common for image by the first camera and image by the second camera.

Also, the first light source may emit illumination light from the inside of the aperture when seen from the subject. In this case, since illumination light for obtaining a light pupil image is emitted from the inside of the aperture by the first light source, the brightness of the pupil of the subject in the light pupil image is more bright and it is possible to detect the pupil of the subject so as to be more conspicuously.

Also, the first light source and the second light source may emit illumination light from the inside of the aperture when seen from the subject. Also in this case, since illumination light for obtaining a light pupil image is emitted from the inside of the aperture by the first light source, the brightness of the pupil of the subject in the light pupil image is more bright and it is possible to detect the pupil of the subject so as to be more conspicuously.

Also, the pupil detection device of the present embodiment may further include a control unit which controls light emission intensities and light emission timings of the first light source, the second light source, and the third light source and an image timing of imaging unit. In this case, by controlling the first light source, the second light source, the third light source, and imaging unit by the control unit, it is possible to make the pupil of the subject more conspicuous and remove a reflection image with glasses, based on the light pupil image and the dark pupil image by the imaging unit, thereby detecting the pupil of the subject more easily.

Also, the control unit may allow the first light source at a first time point, and allow the second light source and the third light source at a second time point different from the first time point. In this case, since it is possible to expand a difference in brightness of a pupil portion between the light pupil image and the dark pupil image by the first light source and the third light source, and generate a reflection image with glasses having brightness, a size and a shape by the second light source, to an extent capable of canceling or removing the glasses-reflective image caused by the first light source using an image difference, by picking up the light pupil image at the first time point at which the first light source emits light and picking up the dark pupil image at the second time point at which the second light source and the third light source emit light, it is possible to make the pupil of the subject more conspicuous and remove the reflection image with glasses by taking a difference between the light pupil image and the dark pupil image, thereby more easily detecting the pupil of the subject.

Also, the control unit may allow the first light source, the second light source, and the third light source to emit light such that a light emission intensity of the first light source at the first time point is equal to the sum of a light emission intensity of the second light source and a light emission intensity of the third light source at the second time point. In this case, since it is possible to equalize brightness of a face portion of the subject or a background in the light pupil image picked up when the first light source is allowed to emit light and the dark pupil image picked up when the second light source and the third light source are allowed to emit light, it is possible to remove the face portion of the subject or the background by taking a difference between the light pupil image and the dark pupil image, thereby easily detecting the pupil of the subject.

Also, the control unit may allow the first light source to emit light and simultaneously the imaging unit to image a light pupil image, allow the second light source to emit light and simultaneously the imaging unit to image a first dark pupil image, allow the third light source to emit light and simultaneously the imaging unit to image a second dark pupil image, and allow the imaging unit to image a non-illumination image in a state where the first light source, the second light source, and the third light source all do not emit light. In this case, by subtracting the non-illumination image from the light pupil image, the first dark pupil image, and the second dark pupil image respectively to take a difference, it is possible to remove influence of external light and, at the same time, detect the pupil of the subject based on the light pupil image, the first dark pupil image and he second dark pupil image even in a state where balance of the light emission intensities of the first light source, the second light source, and the third light source is not achieved.

Also, it may be possible to generate three binarized images in which a pixel value of a portion in which brightness is saturated is set to zero and a pixel value of other portions is set to 1 with respect to the light pupil image, the first dark pupil image and the second dark pupil image, generate a logical product image obtained by taking a logical product of three binarized images, take a logical product between the logical product image and each of the light pupil image, the first dark pupil image, and the second dark pupil image, and detect the pupil of the subject based on the logical product. In this case, since a possibility that a portion in which brightness is saturated is a reflection image with glasses is high, and a pixel value of the portion in which brightness is saturated is zero in the light pupil image, the first dark pupil image, and the second dark pupil image, it is possible to detect the pupil of the subject by setting a pixel value of a portion having a high possibility of being a reflection image with glasses to zero by taking a logical product between the logical product image and each of the light pupil image, the first dark pupil image, and the second dark pupil image. Therefore, it is possible to prevent erroneous detection of the reflection image with glasses as the pupil of the subject.

The illumination light emitted by the first light source may have a first central wavelength, and the illumination light emitted by the second light source and the third light source may have a second central wavelength different from the first central wavelength. The imaging unit may have a first camera, a second camera, and wavelength separating unit which allows light having the first central wavelength to be incident on the first camera and allows light having the second central wavelength to be incident on the second camera. The control unit may allow the first light source, the second light source, and the third light source to emit light simultaneously. In this case, since the wavelength separating unit performs wavelength separation of the light having the first central wavelength and the light having the second central wavelength, the first camera can capture the light pupil image using illumination light which is emitted by the first light source and has the first central wavelength and, at the same time, the second camera can capture the dark pupil images using illumination light which is emitted by the second light source and the third light source and has the second central wavelength. Accordingly, it is possible to prevent an unnecessary difference image from being left in the light pupil image and the dark pupil image by movement of the subject between an image timing of the light pupil image and an image timing of the dark pupil image.

INDUSTRIAL APPLICABILITY

The present invention can expand or maintain brightness/darkness difference between a light pupil image and a dark pupil image and at the same time, remove a reflection image with glasses by using the pupil detection light source device, the pupil detection device, and the pupil detection method.

REFERENCE SIGNS LIST 1 pupil detection device
2 camera (imaging unit)
3A, 3A1, 3A5 light-emitting element (first light source)
3A2, 3A6 light-emitting element (fourth light source)
3B, 3B1, 3B5 light-emitting element (second light source)
3B2, 3C light-emitting element (third light source)
3B6, 3C1 light-emitting element (fifth light source)
3C2, 3C7 light-emitting element (sixth light source)
3C6 light-emitting element (seventh light source)
4 control device (control unit)
6 imaging element
8, 81 aperture (first aperture)
82 aperture (second aperture)

The invention claimed is:

1. A pupil detection light source device which is used for detecting a pupil of a subject based on a light pupil image and a dark pupil image of the subject, and irradiates toward a face of the subject with illumination light for obtaining the light pupil image and the dark pupil image, the pupil detection light source device comprising:
an aperture disposed to face the subject to allow light from a pupil of the subject to pass therethrough, and provided in a camera;
a first light source configured to irradiate toward a face of the subject with illumination light for obtaining the light pupil image by the camera from at least one of inside or vicinity of the aperture when seen from the subject;
a second light source configured to irradiate toward the face of the subject with illumination light for forming a reflection image with glasses to an extent capable of canceling the reflection image with glasses of the subject in the light pupil image obtained by the camera by using an image difference, from a position which exists in at least one of the inside or the vicinity of the aperture when seen from the subject, and at which a distance from a center of the aperture is equal or large in comparison to a position of the first light source; and
a third light source configured to irradiate toward the face of the subject with illumination light for obtaining the dark pupil image by the camera from a position spaced apart from the aperture when seen from the subject.

2. The pupil detection light source device according to claim 1, wherein the second light source emits illumination light having a central wavelength which allows brightness of the pupil of the subject in the dark pupil image to be relatively darker than brightness of the pupil of the subject in the light pupil image.

3. The pupil detection light source device according to claim 1,
wherein the illumination light emitted by the first light source has a first central wavelength, and
the illumination light emitted by the second light source has a second central wavelength longer than the first central wavelength.

4. The pupil detection light source device according to claim 3,
wherein the third light sources emits illumination light having the second central wavelength.

5. The pupil detection light source device according to claim 1,
wherein the third light source is at least a pair of light sources arranged at symmetric positions with the aperture being interposed therebetween.

6. The pupil detection light source device according to claim 1,
wherein the third light source is arranged in a direction away from a center of a visual field of the subject with respect to the second light source when seen from the subject.

7. The pupil detection light source device according to claim 1, further comprising, in a case where the camera is set as a first camera, and an aperture provided in the first camera is set as a first aperture:
a second aperture disposed to face the subject to allow light from a pupil of the subject to pass therethrough, and provided in a second camera; and
a fourth light source configured to irradiate illumination light for obtaining the light pupil image by the second camera toward the face of the subject from at least one of inside or vicinity of the second aperture when seen from the subject,
wherein the third light source irradiates toward the face of the subject with illumination light from a position which exists in at least one of the inside or the vicinity of the second aperture when seen from the subject, and at which a distance from a center of the second aperture is equal or large in comparison to a position of the fourth light source.

8. The pupil detection light source device according to claim 7, further comprising:
a fifth light source configured to irradiate illumination light for obtaining the dark pupil image by the first camera toward the subject from a symmetric position to the third light source with the first aperture being interposed therebetween; and
a sixth light source configured to irradiate illumination light for obtaining the dark pupil image by the second camera toward the subject from a symmetric position to the second light source with the second aperture being interposed therebetween.

9. The pupil detection light source device according to claim 1, further comprising, in a case where the camera is set as a first camera, and an aperture provided in the first camera is set as a first aperture:
a second aperture disposed to face the subject to allow light from a pupil of the subject to pass therethrough, and provided in a second camera;
a fourth light source configured to irradiate illumination light for obtaining the light pupil image by the second camera toward the face of the subject from at least one of inside or vicinity of the second aperture when seen from the subject;
a fifth light source configured to irradiate illumination light for forming a reflection image with glasses to an extent capable of canceling the reflection image with glasses of the subject in the light pupil image obtained by the second camera by using an image difference, toward the subject from a position which exists in at least one of the inside or the vicinity of the second aperture when seen from the subject, and at which a distance from a center of the second aperture is equal or large in comparison to a position of the fourth light source;

a sixth light source configured to irradiate illumination light for obtaining the dark pupil image by the first camera and the second camera toward the face of the subject from a position which is between the first aperture and the second aperture, and at which a distance from the first aperture is equal to a distance from the second aperture; and a seventh light source configured to irradiate illumination light for obtaining the dark pupil image by the second camera toward the face of the subject from a symmetric position to the sixth light source with the second aperture being interposed therebetween, which is a position spaced apart from the second aperture when seen from the subject, wherein the third light source irradiates illumination light from a symmetric position to the sixth light source with the first aperture being interposed therebetween.

10. The pupil detection light source device according to claim 1, wherein the first light source emits illumination light from the inside of the aperture when seen from the subject.

11. The pupil detection light source device according to claim 1, wherein the first light source and the second light source emit illumination light from the inside of the aperture when seen from the subject.

12. A pupil detection device comprising:

a pupil detection light source device according to claim 1;

an imaging unit configured to image a light pupil image and a dark pupil image of the subject obtained by illumination light emitted by the pupil detection light source device; and a pupil detection unit configured to detect a pupil of the subject based on the light pupil image and the dark pupil image, wherein the imaging unit has:

an imaging element configured to image the light pupil image and the dark pupil image, and output image data, and an optical system configured to form the light pupil image and the dark pupil image toward the imaging element.

13. The pupil detection device according to claim 12, further comprising a control unit configured to control light emission intensities and light emission timings of the first light source, the second light source, and the third light source, and an image timing of the imaging unit.

14. The pupil detection device according to claim 13, wherein the control unit allows the first light source to emit light at a first time point, and allows the second light source and the third light source to emit light at a second time point different from the first time point.

15. The pupil detection device according to claim 14, wherein the control unit allows the first light source, the second light source, and the third light source to emit light such that a light emission intensity of the first light source at the first time point is equal to a sum of a light emission intensity of the second light source and a light emission intensity of the third light source at the second time point.

16. The pupil detection device according to claim 13, wherein the control unit allows the first light source to emit light and simultaneously allows the imaging unit to image a light pupil image, allows the second light source to emit light and simultaneously allows the imaging unit to image a first dark pupil image, allows the third light source to emit light and simultaneously allows the imaging unit to image a second dark pupil image, and allows the imaging unit to image a non-illumination image in a state where the first light source, the second light source, and the third light source all do not emit light.

17. The pupil detection device according to claim 16, wherein the pupil detection device generates three binarized images in which a pixel value of a portion in which brightness is saturated is set to zero and a pixel value of other portions is set to 1 with respect to the light pupil image, the first dark pupil image, and the second dark pupil image, generates a logical product image obtained by taking a logical product of the three binarized images, takes a logical product between the logical product image and each of the light pupil image, the first dark pupil image, and the second dark pupil image, and detects the pupil of the subject based on the logical product.

18. The pupil detection device according to claim 13, wherein the illumination light emitted by the first light source has a first central wavelength, the illumination light emitted by the second light source and the third light source has a second central wavelength different from the first central wavelength, the imaging unit has a first camera, a second camera, and a wavelength separating unit which allows light having the first central wavelength to be incident on the first camera and simultaneously allows light having the second central wavelength to be incident on the second camera, and the control unit allows the first light source, the second light source, and the third light source to emit light simultaneously.

19. A pupil detection method using a pupil detection light source device according to claim 1, the pupil detection method comprising:

a step of picking up a light pupil image and a dark pupil image of the subject obtained by illumination light emitted by the pupil detection light source device; and a step of detecting a pupil of the subject based on the light pupil image and the dark pupil image.

* * * * *